United States Patent

Inui et al.

[11] Patent Number: 5,874,494
[45] Date of Patent: Feb. 23, 1999

[54] PHOSPHITES, PROCESS FOR PRODUCING THEM AND THEIR USE

[75] Inventors: Naoki Inui, Nara; Taketoshi Kikuchi; Kanako Fukuda, both of Osaka; Takashi Sanada, Chiba, all of Japan

[73] Assignee: Sumitomo Chemical Company, Limited, Osaka, Japan

[21] Appl. No.: 917,486

[22] Filed: Aug. 26, 1997

[30] Foreign Application Priority Data

Aug. 27, 1996 [JP] Japan ................................. 8-225141
Sep. 25, 1996 [JP] Japan ................................. 8-252924
Sep. 26, 1996 [JP] Japan ................................. 8-254485

[51] Int. Cl.$^6$ .......................... C08K 5/526; C07F 9/145; C07F 9/6574; C07F 9/6578

[52] U.S. Cl. .......................... 504/117; 524/119; 524/128; 524/150; 524/151; 524/152; 558/78; 558/85; 558/158; 558/166; 558/183; 252/400.21; 252/400.24

[58] Field of Search ................................. 524/128, 150, 524/151, 152, 117; 558/158, 166, 183, 85

[56] References Cited

FOREIGN PATENT DOCUMENTS

05086084 A   6/1993   Japan .

*Primary Examiner*—Michael G. Ambrose
*Attorney, Agent, or Firm*—Pillsbury Madison & Sutro

[57] ABSTRACT

Phosphites which are useful as a deterioration inhibitor for organic material and are represented by the following formula:

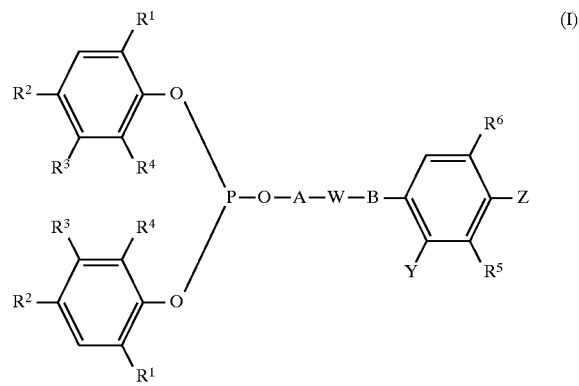

(I)

wherein $R^1$, $R^2$, $R^5$ and $R^6$ represent a hydrogen atom, an alkyl group, a cycloalkyl group, an alkylcycloalkyl group, an aralkyl group or a phenyl group;

$R^3$ represents hydrogen atom or an alkyl group;

$R^4$ represents a hydrogen atom, an alkyl group, a cycloalkyl group, an alkylcycloalkyl group, an aralkyl group or a phenyl group, or the two $R^4$ together form a direct bond, a group represented by —S— or an optionally substituted methylene group;

A represents an alkylene group;

W represents a group represented by —O— or a group represented by —$NR^7$
wherein $R^7$ represents a hydrogen atom, an alkyl group, etc.;

B represents an alkylene group;
and one of Y and Z represents a hydroxyl group, an alkoxy group or an aralkyloxy group, and the other one represents hydrogen atom or an alkyl group.

12 Claims, No Drawings

PHOSPHITES, PROCESS FOR PRODUCING THEM AND THEIR USE

FIELD OF THE INVENTION

The present invention relates to novel phosphites, process for producing them and their use as a stabilizer for organic materials.

BACKGROUND OF THE INVENTION

It has been known that organic materials such as thermoplastic resin, thermosetting resin, natural or synthetic rubber, mineral oil, lubricating oil, adhesive, paint, etc. are deteriorated by the action of, for example, heat, oxygen, etc. on production, processing and use, resulting in lowering of the strength of the organic material due to a phenomenon (e.g. molecular cleavage, molecular crosslinking, etc.), change in flow properties, coloring, deterioration of surface physical properties, etc., which results in a decrease in a commercial value. It has hitherto been known that organic materials may be stabilized by containing various phenol and phosphorous antioxidants for the purpose of solving these problems about heat deterioration and oxidation deterioration.

As the phosphorous antioxidant, for example, tris(2,4-di-t-butylphenyl)phosphite is used.

However, these known phosphorous antioxidants had a problem that the stabilizing effect to heat deterioration and oxidation deterioration is insufficient.

On the other hand, as those for solving the problem of the phosphorous antioxidant, there is suggested, for example, a cyclic phosphite having a carbonyloxy alkylene group, such as 2,10-dimethyl-4,8-di-t-butyl-6-{2-[3-(3-t-butyl-4-hydroxy-5-methylphenyl)propionyloxy]ethoxy}-12H-dibenzo[d,g][1,3,2]dioxaphosphosine, etc. (JP-A-5-86084).

Although these cyclic phosphite exhibits improved stabilizing effects to heat deterioration and oxidation deterioration, these effects are not fully satisfactory. Accordingly, more efficient antioxidant has been desired.

The present inventors have produced various phosphorous compounds and studied intensively. As a result, it has been found that specific cyclic phosphites having an aminoalkylene or oxyalkylene group in place of a carbonyloxy alkylene group exhibits excellent stabilizing effect. It has also been found that specific cyclic phosphites having an oxyalkylene group in place of a carbonyloxy alkylene group exhibits excellent discoloration-resistant effect. Thus, the present invention has been accomplished.

SUMMARY OF THE INVENTION

The present invention provides a phosphite represented by the formula (I):

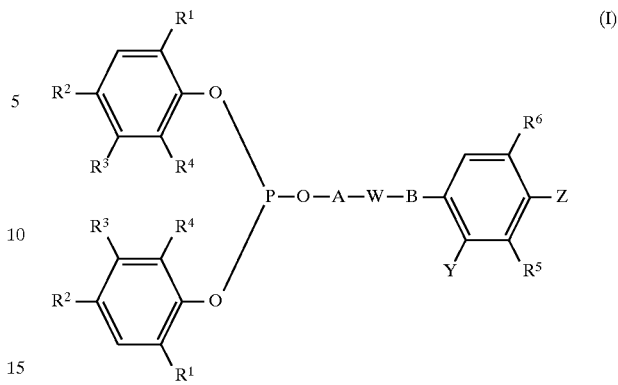

wherein $R^1$, $R^2$, $R^5$ and $R^6$ independently represent a hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group; $R^3$ represents hydrogen atom or an alkyl group having 1 to 8 carbon atoms; $R^4$ represents a hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group, or the two $R^4$ together form a direct bond, a group represented by —S— or a methylene group which may optionally be substituted with alkyl having 1 to 8 carbon atoms or cycloalkyl having 5 to 8 carbon atoms; A represents an alkylene group having 2 to 8 carbon atoms; W represents a group represented by —O— or a group represented by —NR⁷ wherein $R^7$ represents a hydrogen atom, an alkyl group having 1 to 8 carbon atoms or a group represented by the following formula (IX):

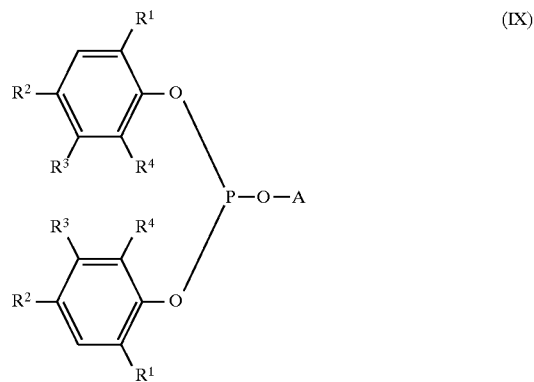

wherein $R^1$, $R^2$, $R^3$, $R^4$ and A are as defined above; B represents an alkylene group having 1 to 8 carbon atoms; and one of Y and Z represents a hydroxyl group, an alkoxy group having 1 to 8 carbon atoms or an aralkyloxy group having 7 to 12 carbon atoms, and the other one represents hydrogen atom or an alkyl group having 1 to 8 carbon atoms.

The present invention also provides a process for producing the phosphites represented by the formula (I) and their use.

DETAILED DESCRIPTION OF THE INVENTION

In the phosphites represented by the formula (I) of the present invention, substituents $R^1$, $R^2$, $R^5$ and $R^6$ independently represent a hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group. Preferably, $R^1$, $R^2$, $R^5$ and $R^6$, which are the same or different each other, are an alkyl group having 1 to 8 carbon atoms, a cycloalkyl group having 5 to 8 carbon atoms or an alkylcycloalkyl group having 6 to 12 carbon atoms.

Typical examples of the alkyl group having 1 to 8 carbon atoms include methyl, ethyl, n-propyl, i-propyl, n-butyl, i-butyl, sec-butyl, t-butyl, t-pentyl, i-octyl, t-octyl and 2-ethylhexyl.

Typical examples of the cycloalkyl group having 5 to 8 carbon atoms include cyclopentyl, cyclohexyl, cycloheptyl and cyclooctyl.

Typical examples of the alkylcycloalkyl group having 6 to 12 carbon atoms include 1-methylcyclopentyl, 1-methylcyclohexyl and 1-methyl-4-i-propylcyclohexyl.

Typical examples of the aralkyl group having 7 to 12 carbon atoms include benzyl, α-methylbenzyl and α,α-dimethylbenzyl.

It is particularly preferred that $R^1$ is a t-alkyl group such as t-butyl, t-pentyl and t-octyl. $R^2$ is preferably an alkyl group having 1 to 5 carbon atoms such as methyl, ethyl, n-propyl, i-propyl, n-butyl, i-butyl, sec-butyl, t-butyl and t-pentyl. Particularly methyl, t-butyl or t-pentyl is preferred as $R^2$. $R^5$ is preferably methyl, t-butyl, t-pentyl and t-octyl. $R^6$ is preferably a hydrogen atom, methyl, t-butyl, t-pentyl and t-octyl.

The substituent $R^3$ represents a hydrogen atom or an alkyl group having 1 to 8 carbon atoms. Examples of the alkyl group having 1 to 8 carbon atoms include methyl, ethyl, n-propyl, i-propyl, n-butyl, i-butyl, sec-butyl, t-butyl, t-pentyl, i-octyl, t-octyl and 2-ethylhexyl. It is preferably a hydrogen atom or an alkyl group having 1 to 5 carbon atoms, particularly a hydrogen atom or a methyl group.

$R^4$ represents a hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group, or the two $R^4$ together form a direct bond, a group represented by —S— or a methylene group which may optionally be substituted with alkyl having 1 to 8 carbon atoms or cycloalkyl having 5 to 8 carbon atoms.

Typical examples of the alkyl group having 1 to 8 carbon atoms as $R^4$ include methyl, ethyl, n-propyl, i-propyl, n-butyl, i-butyl, sec-butyl, t-butyl, t-pentyl, i-octyl, t-octyl and 2-ethylhexyl.

Typical examples of the cycloalkyl group having 5 to 8 carbon atoms as $R^4$ include cyclopentyl, cyclohexyl, cycloheptyl and cyclooctyl.

Typical examples of the alkylcycloalkyl group having 6 to 12 carbon atoms as $R^4$ include 1-methylcyclopentyl, 1-methylcyclohexyl and 1-methyl-4-i-propylcyclohexyl.

Typical examples of the aralkyl group having 7 to 12 carbon atoms as $R^4$ include benzyl, α-methylbenzyl and α,α-dimethylbenzyl.

It is preferred that $R^4$ represents a hydrogen atom, a methyl group, a t-alkyl group such as t-butyl, t-pentyl, and t-octyl, or two $R^4$ together form a direct bond, a group represented by —S—, an unsubstituted methylene group or a methylene group substituted with methyl, ethyl, n-propyl, i-propyl, n-butyl, i-butyl, t-butyl and the like.

The linking group A represents an alkylene group having 2 to 8 carbon atoms. Examples of the alkylene group having 2 to 8 carbon atoms as A include ethylene, propylene, butylene, pentamethylene, hexamethylene, octamethylene and 2,2-dimethyl-1,3-propylene. Preferably, A is ethylene or propylene.

The linking group w represents a group represented by —O— or a group represented by —$NR^7$ wherein $R^7$ represents a hydrogen atom, an alkyl group having 1 to 8 carbon atoms or a group represented by the formula (IX).

Typical examples of the alkyl group having 1 to 8 carbon atoms as $R^7$ include methyl, ethyl, n-propyl, i-propyl, n-butyl, i-butyl, sec--butyl, t-butyl, t-pentyl, i-octyl, t-octyl and 2-ethylhexyl. Preferably, $R^7$ is a hydrogen atom, methyl, ethyl, t-butyl, a group represented by the formula (IX), or the like.

The linking group B represents an alkylene group having 1 to 8 carbon atoms. Examples of the alkylene group having 1 to 8 carbon atoms as B include methylene, ethylene, propylene, butylene, pentamethylene, hexamethylene, octamethylene and 2,2-dimethyl-1,3-propylene. Preferably, B is methylene.

One of Y and Z represents a hydroxy group, an alkoxy group having 1 to 8 carbon atoms or an aralkyloxy group having 7 to 12 carbon atoms, and the other one represents hydrogen atom or an alkyl group having 1 to 8 carbon atoms. Z is preferably an alkoxy group having 1 to 8 carbon atoms or an aralkyloxy group having 7 to 12 carbon atoms.

Examples of the alkyl group having 1 to 8 carbon atoms include methyl, ethyl, n-propyl, i-propyl, n-butyl, i-butyl, sec-butyl, t-butyl, t-pentyl, i-octyl, t-octyl and 2-ethylhexyl.

Examples of the alkoxy group having 1 to 8 carbon atoms include alkoxy group whose alkyl moiety is methyl, ethyl, n-propyl, i-propyl, n-butyl, i-butyl, sec-butyl, t-butyl, t-pentyl, i-octyl, t-octyl or 2-ethylhexyl.

Examples of the aralkyloxy group having 7 to 12 carbon atoms include aralkyloxy group whose aralkyl moiety is methyl, ethyl, n-propyl, i-propyl, n-butyl, i-butyl, sec-butyl, t-butyl, t-pentyl, i-octyl, t-octyl or 2-ethylhexyl.

It is preferred that one of Y and Z is a hydroxy group or a methoxy group.

When W in the formula (I) is a group represented by —O—, the phosphite of formula (I) can be produced, for example, by reacting a phenol or a bisphenol represented by the formula (II):

wherein $R^1$, $R^2$, $R^3$ and $R^4$ are as defined above and phosphorous trihalide with an alcohol represented by the formula (III):

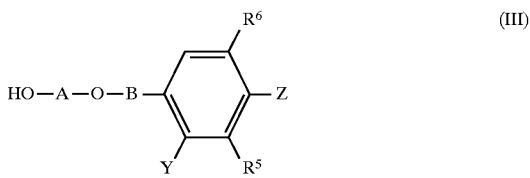

wherein $R^5$, $R^6$, A, B, Y and Z are as defined above.

When W in the formula (I) is a group represented by —$NR^7$—, the phosphite of formula (I) can be produced, for example, by reacting a phenol or a bisphenol represented by the formula (II):

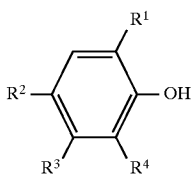

wherein $R^1$, $R^2$, $R^3$ and $R^4$ are as defined above and phosphorous trihalide with an alcohol represented by the formula (IV):

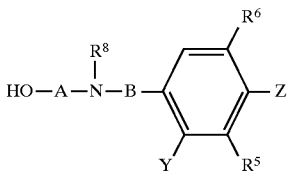

wherein $R^8$ is a hydrogen atom, an alkyl group having 1–8 carbon atoms or a group represented by —AOH, and $R^5$, $R^6$, A, B, Y and Z are as defined above.

Examples of the phosphorous trihalide used either in the reaction when Z represents —$A^1$—CO—O—$Y^1$ wherein $A^1$ and $Y^1$ are as defined above or in the reaction when Z represents —$A^2$—O—CO—$Y^2$ wherein $A^2$ and $y^2$ are as defined above include phosphorous trichloride, phosphorous tribromide and the like. Particularly, phosphorous trichloride is preferred.

The above two reactions can be promoted, for example, by co-presence of a dehydrohalogenation agent such as an amine, a pyridine, a pyrrolidine and an amide, or a hydroxide of an alkali metal or alkaline earth metal.

The amine may be primary amine, secondary amine and tertiary amine. Examples of the amines include t-butylamine, t-pentylamine, t-hexylamine, t-octylamine, di-t-butylamine, di-t-pentylamine, di-t-hexylamine, di-t-octylamine, trimethylamine, triethylamine, N,N-dimethylaniline, N,N-diethylaniline and the like. Among them, triethylamine is preferred.

Examples of the pyridines include pyridine, picoline and the like. Among them, pyridine is preferred. Examples of the pyrrolidines include 1-methyl-2-pyrrolidine and the like.

Examples of the amides include N,N-dimethylformamide, N,N-dimethylacetylamide and the like. Among them, N,N-dimethylformamide is preferred.

Examples of the hydroxide of the alkali metal or alkaline earth metal include sodium hydroxide, calcium hydroxide and the like. Among them, sodium hydroxide is preferred.

The reaction is normally conducted in an organic solvent. The organic solvent may be any one which does not inhibit the reaction, and is not specifically limited. Examples thereof include aromatic hydrocarbon, aliphatic hydrocarbon, oxygen-containing hydrocarbon, halogenated hydrocarbon and the like.

Examples of the aromatic hydrocarbon include benzene, toluene, xylene, ethylbenzene and the like. Examples of the aliphatic hydrocarbon include n-hexane, n-heptane, n-octane and the like. Examples of the oxygen-containing hydrocarbon include diethyl ether, dibutyl ether, tetrahydrofuran, 1,4-dioxane and the like. Examples of the halogenated hydrocarbon include chloroform, carbon tetrachloride, monochlorobenzene, dichloromethane, 1,2-dichloroethane, dichlorobenzene and the like.

Among them, toluene, xylene, n-hexane, n-heptane, diethyl ether, tetrahydrofuran, 1,4-dioxane, chloroform, dichloromethane and the like are preferred.

As the reaction method, there is normally used a two-stage reaction method in which the phenol or bisphenol represented by the formula (II) is firstly reacted with phosphorous trihalide to form an intermediate and then the intermediate is reacted with the alcohol compound (III) or the alcohol compound (IV).

When a phenol is used as the compound of formula (II), phosphorous trihalide is preferably used in an amount of about 0.5 to 0.55 mol, more preferably about 0.5 to 0.52 mol, per mol of the phenol (II). When a bisphenol is used as the compound of formula (II), phosphorous trihalide is preferably used in an amount of about 1 to 1.1 mol, more preferably about 1 to 1.05 mol, per mol of the bisphenols (II).

When using the dehydrohalogenation agent, it is preferably used in an amount of about 0.05 to 2.4 mol, more preferably about 2 to 2.1 mol, per mol of phosphorous trihalide.

The reaction between the bisphenol (II) and phosphorous trihalide is normally carried out at about 0° to 200° C. It is believed that an intermediate halogenophosphite is produced by this reaction. The intermediate may be applied to the following reaction after isolation but is normally applied, as the reaction mixture, to the following reaction, i.e. the reaction between the intermediate and the alcohol compound (III) or the alcohol compound (IV).

In the reaction between the intermediate and the alcohol compound (III), when a phenol is used as the compound of formula (II), the alcohol compound is normally used in an amount of about 0.5 to 0.55 mol per mol of the phenol (II).

In the reaction between the intermediate and the alcohol compound (III), when a bisphenol is used as the compound of formula (II), the alcohol compound is normally used in an amount of about 1 to 1.1 mol per mol of the bisphenol (II).

In the reaction between the intermediate and the alcohol compound (III) the dehydrohalogenation agent can be used. In that case, an amount of the dehydrohalogenation agent is preferably about 0.05 to 1.2 mol per mol of the alcohol compound (III). When using the excess dehydrohalogenation agent in the first stage of reaction, the amount of the dehydrohalogenation agent to be added in the second stage is normally calculated taking the amount of the remained dehydrohalogenation agent into consideration.

The reaction between the intermediate and the alcohol compound (III) is normally carried out at the temperature of about room temperature to 200° C.

In the reaction between the intermediate and the alcohol compound (IV), when $R^8$ in the formula (IV) is a hydrogen atom or an alkyl group having 1–8 carbon atoms, the alcohol compound is normally used in an amount of about 0.9 to 1.1 mol per mol of phosphorous trihalide.

In the reaction between the intermediate and the alcohol compound (IV), when $R^8$ in the formula (IV) represent a group of —AOH, the alcohol compound is normally used in an amount of about 0.45 to 0.55 mol per mol of phosphorous trihalide.

In the reaction between the intermediate and the alcohol compound (IV), the dehydrohalogenation agent can be used. In that case, an amount of the dehydrohalogenation agent is preferably about 0.04 to 1.3 mol per mol of phosphorous trihalide. When using the excess dehydrohalogenation agent in the first stage of reaction, the amount of the dehydrohalogenation agent to be added in the second stage is normally calculated taking the amount of the remained dehydrohalogenation agent into consideration.

The reaction between the intermediate and the alcohol compound (IV) is normally carried out at the temperature of about room temperature to 200° C.

After the completion of the reaction between the intermediate and the alcohol compound (III) or the reaction between the intermediate and the alcohol compound (IV), when using the dehydrohalogenation agent, the phosphites (I) of the present invention can be obtained by removing a hydrogen halogenide of the dehydrohalogenation agent, which is formed in the reaction, removing the solvent and subjecting to a suitable post treatment such as crystallization, column chromatography and the like.

Examples of the phenol (II) include 2-methylphenol, 4-methylphenol, 2,4-dimethylphenol, 2,6-dimethylphenol, 2,4,6-trimethylphenol, 2-ethylphenol, 4-ethylphenol, 2,4-diethylphenol, 2,6-diethylphenol, 2,4,6-triethylphenol, 2-t-butylphenol, 4-t-butylphenol, 2-t-butyl-4-methylphenol, 2-t-butyl-5-methylphenol, 2-t-butyl-4-ethylphenol, 2,4-di-t-butylphenol, 2-t-butyl-6-methylphenol, 2-t-butyl-6-ethylphenol, 2,6-di-t-butylphenol, 2,4-dimethyl-6-t-butylphenol, 2,6-dimethyl-4-t-butylphenol, 2-methyl-4,6-di-t-butylphenol, 3-methyl-4,6-di-t-butylphenol, 2-ethyl-4,6-di-t-butylphenol, 3-ethyl-4,6-di-t-butylphenol, 4-methyl-2,6-di-t-butylphenol, 4-ethyl-2,6-di-t-butylphenol, 2,4,6-tri-t-butylphenol, 2,4-di-t-pentylphenol, 2-t-octylphenol, 2,4-di-t-octylphenol, 2,6-di-t-octylphenol, 2,4,6-tri-t-octylphenol, 2-nonylphenol, 4-nonylphenol, 2-cyclohexyl-4-methylphenol and 2-(1-methylcyclohexyl)-4-methylphenol.

Examples of the bisphenol (II) include 2,2'-methylenebis(4-methyl-6-t-butylphenol), 2,2'-methylenebis(4-ethyl-6-t-butylphenol), 2,2'-methylenebis(4-n-propyl-6-t-butylphenol), 2,2'-methylenebis(4-i-propyl-6-t-butylphenol), 2,2'-methylenebis(4-n-butyl-6-t-butylphenol), 2,2'-methylenebis(4-i-butyl-6-t-butylphenol), 2,2'-methylenebis(4,6-di-t-butylphenol), 2,2'-methylenebis(4-t-pentyl-6-t-butylphenol), 2,2'-methylenebis(4-nonyl-6-t-butylphenol), 2,2'-methylenebis(4-t-octyl-6-t-butylphenol), 2,2'-methylenebis(4-methyl-6-t-pentylphenol), 2,2'-methylenebis(4-methyl-6-cyclohexylphenol), 2,2'-methylenebis[4-methyl-6-(α-methylcyclohexyl)phenol)], 2,2'-methylenebis(4-methyl-6-t-nonylphenol), 2,2-methylenebis(4-methyl-6-t-octylphenol), 2,2'-methylenebis (4,6-di-t-pentylphenol), 2,2'-methylenebis[4-nonyl-6-(α-methylbenzyl)phenol], 2,2'-methylenebis[4-nonyl-6-(α,α-dimethylbenzyl)phenol], 2,2'-ethylidenebis(4-methyl-6-butylphenol), 2,2'-ethylidenebis(4-ethyl-6-t-butylphenol), 2,2'-ethylidenebis(4-n-propyl-6-t-butylphenol), 2,2'-ethylidenebis(4-i-propyl-6-t-butylphenol), 2,2'-ethylidenebis(4-n-butyl-6-t-butylphenol), 2,2'-ethylidenebis(4-i-butyl-6-t-butylphenol), 2,2'-ethylidenebis(4,6-di-t-butylphenol), 2,2'-ethylidenebis(4-t-pentyl-6-t-butylphenol), 2,2'-ethylidenebis(4-nonyl-6-t-butylphenol), 2,2'-ethylidenebis(4-t-octyl-6-t-butylphenol), 2,2'-ethylidenebis(4-methyl-6-t-pentylphenol), 2,2'-ethylidenebis(4-methyl-6-cyclohexylphenol), 2,2'-ethylidenebis[4-methyl-6-(α-methylcyclohexyl)phenol)], 2,2'-ethylidenebis(4-methyl-6-nonylphenol), 2,2'-ethylidenebis(4-methyl-6-t-octylphenol), 2,2'-ethylidenebis (4,6-di-t-pentylphenol), 2,2'-ethylidenebis[4-nonyl-6-(α-methylbenzyl)phenol], 2,2'-ethylidenebis[4-nonyl-6-(α,α-dimethylbenzyl)phenol], 2,2'-propylidenebis(4-methyl-6-t-butylphenol), 2,2'-propylidenebis(4-ethyl-6-t-butylphenol), 2,2'-propylidenebis(4-n-propyl-6-t-butylphenol), 2,2'-propylidenebis(4-i-propyl-6-t-butylphenol), 2,2'-propylidenebis(4-n-butyl-6-t-butylphenol), 2,2'-propylidenebis(4-i-butyl-6-t-butylphenol), 2,2'-propylidenebis(4,6-di-t-butylphenol), 2,2'-propylidenebis(4-t-pentyl-6-t-butylphenol), 2,2'-propylidenebis(4-nonyl-6-t-butylphenol), 2,2'-propylidenebis(4-t-octyl-6-t-butylphenol), 2,2'-propylidenebis(4-methyl-6-t-pentylphenol), 2,2'-propylidenebis(4-methyl-6-cyclohexylphenol), 2,2'-propylidenebis[4-methyl-6-(α-methylcyclohexyl)phenol)], 2,2'-propylidenebis(4-methyl-6-nonylphenol), 2,2'-propylidenebis(4-methyl-6-t-octylphenol), 2,2'-propylidenebis(4,6-di-t-pentylphenol), 2,2'-propylidenebis[4-nonyl-6-(α-methylbenzyl)phenol], 2,2'-propylidenebis[4-nonyl-6-(α,α-dimethylbenzyl)phenol], 2,2'-butylidenebis(4-methyl-6-t-butylphenol), 2,2'-butylidenebis(4-ethyl-6-t-butylphenol), 2,2'-butylidenebis(4,6-di-t-butylphenol), 2,2'-butylidenebis(4-methyl-6-cyclohexylphenol), 2,2'-butylidenebis[4-methyl-6-(α-methylcyclohexyl)phenol)], 2,2'-butylidenebis(4,6-di-t-pentylphenol), 2,2'-i-butylidenebis(4-methyl-6-t-butylphenol), 2,2'-i-butylidenebis(4-ethyl-6-t-butylphenol), 2,2'-i-butylidenebis(4,6-di-t-butylphenol), 2,2'-i-butylidenebis(4-methyl-6-cyclohexylphenol), 2,2'-i-butylidenebis[4-methyl-6-(α-methylcyclohexyl)phenol)], 2,2'-i-butylidenebis(4,6-di-t-pentylphenol), 2,2'-i-pentylidenebis(4-methyl-6-t-butylphenol), 2,2'-i-pentylidenebis(4-ethyl-6-t-butylphenol), 2,2'-i-pentylidenebis(4,6-di-t-butylphenol), 2,2'-i-pentylidenebis(4-methyl-6-cyclohexylphenol), 2,2'-pentylidenebis[4-methyl-6-(α-methylcyclohexy)phenol], 2,2'-pentylidenebis (4,6-di-t-pentylphenol), biphenyl-2,2'-diol, 3,3',5,5'-tetra-t-butylbiphenyl-2,2'-diol and 1,1'-binaphthyl-2,2'-diol.

The bisphenol (II) as a raw material of the phosphites (I) can also be produced by condensing alkylphenols according to a known method, for example, methods described in JP-A-52-122350, U.S. Pat. No. 2,538,355 or JP-B-2-47451. As the bisphenols (II), commercially available one can also be used.

When B in the formula (III) is a methylene group, the alcohol compound (III) can be produced, for example, by reacting a hydroxy carboxylic acid represented by the formula (V):

(V)

wherein $R^5$, $R^6$, Y and Z are as defined above with a diol represented by the formula(VI):

HO—A—OH (VI)

wherein A is as defined above and formaldehyde.

When B in the formula (III) is an alkylene group other than methylene, the alcohol compound (III) can be produced, for example, by reacting a halide represented by the formula (VIII):

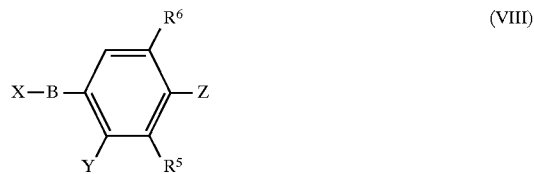

(VIII)

wherein $R^5$, $R^6$, B, Y and Z are as defined above with a diol represented by the formula(VI).

When B in the formula (IV) is a methylene group, the alcohol compound (IV) can be produced, for example, by reacting a hydroxy carboxylic acid represented by the formula (V):

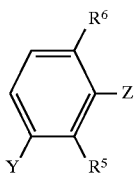

(V)

wherein $R^5$, $R^6$, Y and Z are as defined above with an alkanolimine represented by the formula(VII):

HO—A—NHR$^8$ (VII)

wherein A and $R^8$ are as defined above and formaldehyde.

When B in the formula (IV) is an alkylene group other than methylene, the alcohol compound (IV) can be produced, for example, by reacting a halide represented by the formula (VIII):

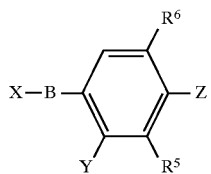

(VIII)

wherein $R^5$, $R^6$, B, Y and Z are as defined above with an alkanolimine represented by the formula(VII).

Examples of the alcohol compound (III) include 2-(3-t-butyl-2-hydroxyphenylmethyloxy)ethanol, 2-(3-t-butyl-4-hydroxyphenylmethyloxy)ethanol, 2-(3-t-butyl-2-hydroxy-5-methylphenylmethyloxy)ethanol, 2-(3,5-di-t-butyl-2-hydroxyphenylmethyloxy)ethanol, 2-(3-t-butyl-4-hydroxy-5-methylphenylmethyloxy)ethanol, 2-(3,5-di-t-butyl-4-hydroxyphenylmethyloxy)ethanol, 2-(2-methyl-3,5-di-t-butyl-4-hydroxyphenylmethyloxy)ethanol, 2-(3-t-butyl-2-methoxyphenylmethyloxy)ethanol, 2-(3-t-butyl-4-methoxyphenylmethyloxy)ethanol, 2-(3-t-butyl-2-methoxy-5-methylphenylmethyloxy)ethanol, 2-(3,5-di-t-butyl-2-methoxyphenylmethyloxy)ethanol, 2-(3-t-butyl-4-methoxy-5-methylphenylmethyloxy)ethanol, 2-(3,5-di-t-butyl-4-methoxyphenylmethyloxy)ethanol, 2-(2-methyl-3,5-di-t-butyl-4-hydroxyphenylmethyloxy)ethanol, 3-(3-t-butyl-2-hydroxyphenylmethyloxy)propanol, 3-(3-t-butyl-4-hydroxyphenylmethyloxy)propanol, 3-(3-t-butyl-2-hydroxy-5-methylphenylmethyloxy)propanol, 3-(3,5-di-t-butyl-4-hydroxyphenylmethyloxy)propanol, 3-(2-methyl-3,5-di-t-butyl-4-hydroxyphenylmethyloxy)propanol, 3-(3-t-butyl-2-methoxyphenylmethyloxy)propanol, 2-(3-t-butyl-4-methoxyphenylmethyloxy)propanol, 2-(3-t-butyl-2-methoxy-5-methylphenylmethyloxy)propanol, 2-(3,5-di-t-butyl-2-methoxyphenylmethyloxy)propanol, 2-(3-t-butyl-4-methoxy-5-methylphenylmethyloxy)propanol, 3-(2-methyl-3,5-di-t-butyl-4-methoxyphenylmethyloxy)propanol, 4-(3-t-butyl-2-hydroxyphenylmethyloxy)butanol, 4-(3-t-butyl-4-hydroxyphenylmethyloxy)butanol, 4-(3-t-butyl-2-hydroxy-5-methylphenylmethyloxy)butanol, 4-(3,5-di-t-butyl-2-hydroxyphenylmethyloxy)butanol, 4-(3-t-butyl-4-hydroxy-5-methylphenylmethyloxy)butanol, 4-(3,5-di-t-butyl-4-hydroxyphenylmethyloxy)butanol, 4-(2-methyl-3,5-di-t-butyl-4-hydroxyphenylmethyloxy)butanol, 4-(3-t-butyl-2-methoxyphenylmethyloxy)butanol, 2-(3-t-butyl-2-methoxy-5-methylphenylmethyloxy)butanol, 2-(3,5-di-t-butyl-2-methoxyphenylmethyloxy)butanol, 2-(3-t-butyl-4-methoxy-5-methylphenylmethyloxy)butanol, 4-(3,5-di-t-butyl-4-methoxyphenylmethyloxy)butanol and 4-(2-methyl-3,5-di-t-butyl-4-methoxyphenylmethyloxy)butanol, As the alcohol compound (III), a commercially available one can also be used.

Examples of the alcohol (IV) include 2-[N-(3-t-butyl-2-hydroxyphenymethyl)amino]ethanol, 2-[N-(3-t-butyl-4-hydroxyphenymethyl)amino]ethanol, 2-[N-(3-t-butyl-2-hydroxy-5-methylphenymethyl)amino]ethanol, 2-[N-(3,5-di-t-butyl-2-hydroxyphenymethyl)amino]ethanol, 2-[N-(3-t-butyl-4-hydroxy-5-methylphenymethyl)amino]ethanol, 2-[N-(3,5-di-t-butyl-4-hydroxyphenymethyl)amino]ethanol, 2-[N-(2-methyl-3,5-di-t-butyl-4-hydroxyphenymethyl)amino]ethanol, 2-[N-(3-t-butyl-2-methoxyphenymethyl)amino]ethanol, 2-[N-(3-t-butyl-4-methoxyphenymethyl)amino]ethanol, 2-[N-(3-t-butyl-2-methoxy-5-methylphenymethyl)amino]ethanol, 2-[N-(3,5-di-t-butyl-2-methoxyphenymethyl)amino]ethanol, 2-[N-(3-t-butyl-4-methoxy-5-methylphenymethyl)amino]ethanol, 2-[N-(3,5-di-t-butyl-4-methoxyphenymethyl)amino]ethanol, 2-[N-(2-methyl-3,5-di-t-butyl-4-methoxyphenymethyl)amino]ethanol, 2-[N-(3-t-butyl-2-hydroxyphenymethyl)-N-methylamino]ethanol, 2-[N-(3-t-butyl-4-hydroxyphenymethyl)-N-methylamino]ethanol, 2-[N-(3-t-butyl-2-hydroxy-5-methylphenymethyl)-N-methylamino]ethanol, 2-[N-(3,5-di-t-butyl-2-hydroxyphenymethyl)-N-methylamino]ethanol, 2-[N-(3-t-butyl-4-hydroxy-5-methylphenymethyl)-N-methylamino]ethanol, 2-[N-(3,5-di-t-butyl-4-hydroxyphenymethyl)-N-methylamino]ethanol, 2-[N-(2-methyl-3,5-di-t-butyl-4-hydroxyphenymethyl)-N-methylamino]ethanol, 2-[N-(3-t-butyl-2-hydroxyphenymethyl)-N-ethylamino]ethanol, 2-[N-(3-t-butyl-4-hydroxyphenymethyl)-N-ethylamino]ethanol, 2-[N-(3-t-butyl-2-hydroxy-5-methylphenymethyl)-N-ethylamino]ethanol, 2-[N-(3,5-di-t-butyl-2-hydroxyphenymethyl)-N-ethylamino]ethanol, 2-[N-(3-t-butyl-4-hydroxy-5-methylphenymethyl)-N-ethylamino]ethanol, 2-[N-(3,5-di-t-butyl-4-hydroxyphenymethyl)-N-ethylamino]ethanol, 2-[N-(2-methyl-3,5-di-t-butyl-4-hydroxyphenymethyl)-N-ethylamino]ethanol, 2-[N-(3-t-butyl-2-hydroxyphenymethyl)-N-t-butylamino]ethanol, 2-[N-(3-t-butyl-4-hydroxyphenymethyl)-N-t-butylamino]ethanol, 2-[N-(3-t-butyl-2-hydroxy-5-methylphenymethyl)-N-t-butylamino]ethanol, 2-[N-(3,5-di-t-butyl-2-hydroxyphenymethyl)-N-t-butylamino]ethanol, 2-[N-(3-t-butyl-4-hydroxy-5-methylphenymethyl)-N-t-butylamino]ethanol, 2-[N-(3,5-di-t-butyl-4-hydroxyphenymethyl)-N-t-butylamino]ethanol, 2-[N-(2-methyl-3,5-di-t-butyl-4-hydroxyphenymethyl)-N-t-butylamino]ethanol, 3-[N-(3-t-butyl-2-hydroxyphenymethyl)amino]propanol, 3-[N-(3-t-butyl-4-hydroxyphenymethyl)amino]propanol, 3-[N-(3-t-butyl-2-hydroxy-5-methylphenymethyl)amino]propanol, 3-[N-(3,5-di-t-butyl-2-hydroxyphenymethyl)amino]propanol, 3-[N-(3-t-butyl-4-hydroxy-5-methylphenymethyl)amino]propanol, 3-[N-(3,5-di-t-butyl-4-hydroxyphenymethyl)amino]propanol, 3-[N-(2-methyl-3,5-di-t-butyl-4-hydroxyphenymethyl)amino]propanol, 3-[N-(3-t-butyl-2-hydroxy-5-methylphenymethyl)-N-methylamino]propanol, 3-[N-(3,5-di-t-butyl-2-hydroxyphenymethyl)-N-methylamino]propanol, 3-[N-(3-t-butyl-4-hydroxy-5-methylphenymethyl)-N-methylamino]propanol, 3-[N-(3,5-di-t-butyl-4-hydroxyphenymethyl)-N-methylamino]propanol, 4-[N-(3-t-butyl-2-hydroxyphenymethyl)amino]butanol, 4-[N-(3-t-butyl-4-hydroxyphenymethyl)amino]butanol, 4-[N-(3-t-butyl-2-hydroxy-5-methylphenymethyl)amino]butanol, 4-[N-(3,5-di-t-butyl-2-hydroxyphenymethyl)amino]butanol, 4-[N-(3-t-butyl-4-hydroxy-5-methylphenymethyl)amino]butanol, 4-[N-(3,5-di-t-butyl-4-hydroxyphenymethyl)amino]butanol, 4-[N-(2-methyl-3,5-di-t-butyl-4-hydroxyphenymethyl)amino]butanol, 4-[N-(3-t-butyl-2-hydroxy-5-methylphenymethyl)-N-methylamino]butanol, 4-[N-(3,5-di-t-butyl-2-hydroxyphenymethyl)-N- methylamino]butanol, 4-[N-(3-t-butyl-4-hydroxy-5-methylphenymethyl)-N-methylamino]butanol, 4-[N-(3,5-di-t-butyl-4-hydroxyphenymethyl)-N-methylamino]butanol, 2,2'-(2-hydroxy-3-t-butylphenylmethyl)iminodiethanol, 2,2'-(2-hydroxy-5-t-butylphenylmethyl)iminodiethanol, 2,2'-(4-hydroxy-3-t-butylphenylmethyl)iminodiethanol, 2,2'-(2-hydroxy-3-t-butyl-5-methylphenylmethyl)iminodiethanol, 2,2'-(2-hydroxy-3-methyl-5-t-butyl-phenylmethyl)iminodiethanol, 2,2'-(4-hydroxy-3-t-butyl-5-methylphenylmethyl)iminodiethanol, 2,2'-(2-hydroxy-3-t-butyl-6-methylphenylmethyl)iminodiethanol, 2,2'-(4-hydroxy-3-t-butyl-6-methylphenylmethyl)iminodiethanol, 2,2'-(2-hydroxy-3,5-di-t-butylphenylmethyl)iminodiethanol, 2,2'-(4-hydroxy-3,5-di-t-butylphenylmethyl)iminodiethanol, 2,2'-(2-hydroxy-3,5-di-t-pentylphenylmethyl)iminodiethanol, 2,2'-(4-hydroxy-3,5-di-t-pentylphenylmethyl)iminodiethanol, 2,2'-(2-hydroxy-3,5-dicyclohexylphenylmethyl)iminodiethanol, 2,2'-(4-hydroxy-3,5-dicyclohexylphenylmethyl)iminodiethanol, 2,2'-[2-hydroxy-3,5-di($\alpha$-methylcyclohexyl)phenylmethyl]iminodiethanol, 2,2'-[4-hydroxy-3,5-di($\alpha$-methylcyclohexyl)phenylmethyl]iminodiethanol, 2,2'-(2-hydroxy-3,5-di-t-butyl-6-methylphenylmethyl)iminodiethanol, 2,2'-(4-hydroxy-3,5-di-t-butyl-6-methylphenylmethyl)iminodiethanol, 3,3'-(2-hydroxy-3-t-butylphenylmethyl)iminodipropanol, 3,3'-(2-hydroxy-5-t-butylphenylmethyl)iminodipropanol, 3,3'-(4-hydroxy-3-t-butylphenylmethyl)iminodipropanol, 3,3'-(2-hydroxy-3-t-butyl-5-methylphenylmethyl)iminodipropanol, 3,3'-(2-hydroxy-3-methyl-5-t-butylphenylmethyl)iminodipropanol, 3,3'-(4-hydroxy-3-t-butyl-5-methylphenylmethyl)iminodipropanol, 3,3'-(2-hydroxy-3-t-butyl-6-methylphenylmethyl)iminodipropanol, 3,3'-(4-hydroxy-3-t-butyl-6-methylphenylmethyl)iminodipropanol, 3,3'-(2-hydroxy-3,5-di-t-butylphenylmethyl)iminodipropanol, 3,3'-(4-hydroxy-3,5-di-t-butylphenylmethyl)iminodipropanol, 3,3'-(2-hydroxy-3,5-di-t-pentylphenylmethyl)iminodipropanol, 3,3'-(4-hydroxy-3,5-di-t-pentylphenylmethyl)iminodipropanol, 3,3'-(2-hydroxy-3,5-dicyclohexylphenylmethyl)iminodipropanol, 3,3'-(4-hydroxy-3,5-dicyclohexylphenylmethyl)iminodipropanol, 3,3'-[2-hydroxy-3,5-di($\alpha$-methylcyclohexyl)phenylmethyl]iminodipropanol, 3,3'-[4-hydroxy-3,5-di($\alpha$-methylcyclohexyl)phenylmethyl]iminodipropanol, 3,3'-(2-hydroxy-3,5-di-t-butyl-6-methylphenylmethyl)iminodipropanol, 3,3'-(4-hydroxy-3,5-di-t-butyl-6-methylphenylmethyl)iminodipropanol, 4,4'-(2-hydroxy-3-t-butylphenylmethyl)iminodibutanol, 4,4'-(2-hydroxy-5-t-butylphenylmethyl)iminodibutanol, 4,4'-(4-hydroxy-3-t-butylphenylmethyl)iminodibutanol, 4,4'-(2-hydroxy-3-t-butyl-5-methylphenylmethyl)iminodibutanol, 4,4'-(2-hydroxy-3-methyl-5-t-butylphenylmethyl)iminodibutanol, 4,4'-(4-hydroxy-3-t-butyl-5-methylphenylmethyl)iminodibutanol, 4,4'-(2-hydroxy-3-t-butyl-6-methylphenylmethyl)iminodibutanol, 4,4'-(4-hydroxy-3-t-butyl-6-methylphenylmethyl)iminodibutanol, 4,4'-(2-hydroxy-3,5-di-t-butylphenylmethyl)iminodibutanol, 4,4'-(4-hydroxy-3,5-di-t-butylphenylmethyl)iminodibutanol, 4,4'-(2-hydroxy-3,5-di-t-pentylphenylmethyl)iminodibutanol, 4,4'-(4-hydroxy-3,5-di-t-pentylphenylmethyl)iminodibutanol, 4,4'-(2-hydroxy-3,5-dicyclohexylphenylmethyl)iminodibutanol, 4,4'-(4-hydroxy-3,5-dicyclohexylphenylmethyl)iminodibutanol, 4,4'-[2-hydroxy-3,5-di($\alpha$-methylcyclohexyl)phenylmethyl]iminodibutanol, 4,4'-[4-hydroxy-3,5-di($\alpha$-methylcyclohexyl)phenylmethyl]iminodibutanol, 4,4'-(2-hydroxy-3 5-di-t-butyl-6-methylphenylmethyl)iminodibutanol and 4,4'-(4-hydroxy-3,5-di-t-butyl-6-methylphenylmethyl)iminodibutanol.

The hydrolysis resistance of the phosphites (I) of the present invention can be improved by containing amines, acid-bonded metal salts and the like.

Typical examples of the amines include trialkanolamines such as triethanolamine, tripropanolamine, tri-i-propanolamine and the like; dialkanolamines such as diethanolamine, dipropanolamine, di-i-propanolamine, tetraethanolethylenediamine, tetra-i-propanolethylenediamine and the like; monoalkanolamines such as dibutylethanolamine, dibutyl-i-propanolamine and the like; aromatic amines such as 1,3,5-trimethyl-2,4,6-triazine and the like; alkylamines such as dibutylamine, piperidine, 2,2,6,6,-tetramethylpiperidine, 4-hydroxy-2,2,6,6-tetramethylpiperidine and the like; polyalkylenepolyamines such as hexamethylenetetramine, triethylenediamine, triethylenetetramine, tetraethylenepentamine and the like; and hindered amine photostabilizers described hereinafter.

Furthermore, there can also be used a long-chain aliphatic amine described in JP-A-61-63686, a compound having a steric hindrance amine group described in JP-A-6-329830, a hindered piperidinyl photostabilizer described in JP-A-7-90270 and an organic amine described in JP-A-7-278164.

The amines are normally used in an amount of about 0.01 to 25% by weight based on the amount of phosphite (I).

Typical examples of the acid-bonded metal salt include hydrotalcites. Examples of the hydrotalcites include double salt compounds represented by the following formula:

$$M^{2+}_{1-x} \cdot M^{3+}_{x} \cdot (OH^-)_2 \cdot (A^{n-})_{x/n} \cdot pH_2O$$

wherein $M^{2+}$ represents $Mg^{2+}$, $Ca^{2+}$, $Sr^{2+}$, $Ba^{2+}$, $Zn^{2+}$, $Pb^{2+}$, $Sn^{2+}$ and/or $Ni^{2+}$; $M^{3+}$ represents $Al^{3+}$, $B^{3+}$ or $Bi^{3+}$; n represents a numerical value of 1 to 4; x represents a numerical value of 0 to 0.5; p represents a numerical value of 0 to 2; and $A^{n-}$ represents an anion having a valency of n.

Specific examples of the amino having a valence of n represented by $A^{n-}$ include $OH^-$, $Cl^-$, $Br^-$, $I^-$, $ClO_4^-$, $HCO_3^-$, $C_6H_5COO^-$, $CO_3^{2-}$, $SO^{2-}$, $-OOCCOO-$, $(CHOHCO)_2^{2-}$, $C_2H_4(COO)_2^{2-}$, $(CH_2COO)_2^{2-}$, $CH_3CHOHCOO-$, $SiO_3^{2-}$, $SiO_4^{4-}$, $Fe(CN)_6^{4-}$, $BO_3^{3-}$, $PO_3^{3-}$, $HPO_4^{2-}$ and the like.

Among those represented by the above formula, particularly preferred include, for example, hydrotalcites represented by the following formula:

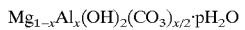

$$Mg_{1-x}Al_x(OH)_2(CO_3)_{x/2} \cdot pH_2O$$

wherein x and p are as defined above.

The hydrotalcites may be natural or synthetic products, and can be used regardless of crystal structure and crystal particle diameter thereof.

Furthermore, an ultrafine zinc oxide described in JP-A-6-329830 and an inorganic compound described in JP-A-7-278164 can also be used.

The acid-bonded metal salt to is normally used in an amount of about 0.01 to 25% by weight based on the amount of phosphite (I).

The phosphites (I) of the present invention are effective for stabilizing the organic material against heat deterioration and oxidation deterioration. Examples of the organic material which can be stabilized by phosphites (I) of the present invention include the following. They can be stabilized alone or in combination thereof. The organic material which can be stabilized by phosphites (I) of the present invention are not limited to these organic materials.

(1) polyethylene, for example, high-density polyethylene (HD-PE), low-density polyethylene (LD-PE) and straight-chain low-density polyethylene (LLDPE)
(2) polypropylene
(3) methylpentene polymer
(4) EEA (ethylene/ethyl acrylate copolymer) resin
(5) ethylene/vinyl acetate copolymer resin
(6) polystyrenes, for example, polystyrene, poly(p-methylstyrene) and poly(α-methylstyrene)
(7) AS (acrylonitrile/styrene copolymer) resin
(8) ABS (acrylonitrile/butadiene/styrene copolymer) resin
(9) AAS (special acrylic rubber/acrylonitrile/styrene copolymer) resin
(10) ACS (acrylonitrile/chlorinated polyethylene/styrene copolymer) resin
(11) chlorinated polyethylene, polychloroprene, chlorinated rubber
(12) polyvinyl chloride, polyvinylidene chloride
(13) methacrylic resin
(14) ethylene/vinyl alcohol copolymer resin
(15) fluororesin
(16) polyacetal
(17) grafted polyphenylene ether resin and polyphenylene sulfide resin
(18) polyurethane
(19) polyamide
(20) polyester resin, for example, polyethylene terephthalate and polybutylene terephthalate
(21) polycarbonate
(22) polyacrylate
(23) polysulfone, polyether ether ketone, polyether sulfone
(24) thermoplastic resin such as aromatic polyester resin, etc.
(25) epoxy resin
(26) diallyl phthalate prepolymer
(27) silicone resin
(28) unsaturated polyester resin
(29) acrylic-modified benzoguanamine resin
(30) benzoguanamine/melamine resin
(31) thermosetting resin such as urea resin, etc.
(32) polybutadiene
(33) 1,2-polybutadiene
(34) polyisoprene
(35) styrene/butadiene copolymer
(36) butadiene/acrylonitrile copolymer
(37) ethylene/propylene copolymer
(38) silicone rubber
(39) epichlorohydrin rubber
(40) acrylic rubber
(41) natural rubber
(42) chlorinated rubber paint
(43) polyester resin paint
(44) urethane resin paint
(45) epoxy resin paint
(46) acrylic resin paint
(47) vinyl resin paint
(48) aminoalkyd resin paint
(49) alkyd resin
(50) nitrocellulose resin paint
(51) oil-based paint
(52) wax
(53) lubricating oil, etc.

Among them, the thermoplastic resin, particularly polyolefin such as polyethylene (e.g. HD-PE, LD-PE, LLDPE, etc.) and polyolefin (e.g. polypropylene, etc.), and the engineering resin such as polyamide, polyethylene terephthalate, polybutylene terephthalate and polycarbonate, are more suitable to be stabilized by phosphites (I) of the present invention.

The polyolefins are not specifically limited. For example, they may be those obtained by the radical polymerization or those produced by the polymerization using a catalyst containing a metal of Group IVb, Vb, VIb or VIII of the periodic table. The catalyst containing such a metal may be a metal complex which is coordinated by one or more ligands, for example, oxide which is coordinated by a π or σ bond, halogenated compound, alcoholate, ester, aryl and the like, and these complexes may be used as they are, or a base material such as magnesium chloride, titanium chloride, alumina, silicon oxide, etc. may carry the complexes.

As the polyolefin, for example, there are preferably used those produced by using Ziegler-Natta catalyst, TNZ catalyst, metallocene catalyst, Phillips catalyst and the like.

Also the engineering resin is not specifically limited. The polyamide resin, an example of the engineering resins, may be those which have an amide bond at the polymer chain and can be molten with heating. For example, they may be produced by any method such as condensation reaction between diamines and dicarboxylic acids, condensation reaction of aminocarboxylic acids and ring opening polymerization of lactams. Typical examples thereof include nylon 66, nylon 69, nylon 610, nylon 612, poly-bis(p-aminocyclohexyl)methanedodecamide, nylon 46, nylon 6, nylon 12 and copolymers (e.g. nylon 66/6 as a copolymer of nylon 66 and nylon 6, nylon 6/12, etc.).

The polyester resin may be those which have an ester bond in the polymer chain and can be molten with heating, and examples thereof include polyester obtained by the polycondensation between dicarboxylic acids and a dihydroxy compound. The polyester may be a homopolyester or a copolyester.

The polycarbonate may be those which have a carbonate bond in the polymer chain and can be molten with heating, and examples thereof include polycarbonate obtained by reacting an aromatic hydroxyl compound and/or a small amount of polyhydroxy compound with a carbonate precursor such as phosgene, diphenyl carbonate, etc. in the presence of a solvent, an acid receptor and a molecular weight adjustor. The polycarbonate resin may be straight-chain or branched resin, or may be a copolymer.

When the organic material is stabilized by containing the phosphites (I) of the present invention, the phosphites (I) are normally formulated in an amount of about 0.01 to 5 parts by weight, preferably about 0.03 to 3 parts by weight, more preferably about 0.05 to 1 parts by weight, based on 100 parts by weight of the organic material. When the amount is less than 0.01 parts by weight, the stabilizing effect may not be sufficient, necessarily. On the other hand, even when the amount exceeds 5 parts by weight, an improvement of the effect corresponding to the increase in the amount used may not be obtained and this may be economically disadvantageous.

When the phosphites (I) of the present invention are contained in the organic material, if desired, there can also be contained one or more other additives such as phenol antioxidant, sulfur antioxidant, phosphorous antioxidant, ultraviolet absorber, photostabilizer, peroxide scavenger, polyamide stabilizer, hydroxylamine, lubricant, plasticizer, flame retardant, nucleating agent, metal inactivating agent, antistatic agent, pigment, filler, pigment, anti-blocking agent, surfactant, processing aid, foaming agent, emulsifier, brightener, calcium stearate, neutralizing agent (e.g. hydrotalcite, etc.), coloring modifier (e.g. 9,10-dihydro-oxa-10-phosphophenanthrene-10-oxide, etc.) and co-stabilizer (e.g. benzofurans, indolines, etc. described in U.S. Pat. Nos. 4,325,853, 4,338,244, 5,175,312, 5,216,053, 5,252,643 and 4,316,611, DE-A-4,316,622 and 4,316,876, and EP-A-589, 839 and 591,101). These additives can be formulated together with the phosphite (I), and/or can be formulated in the stage other than a stage where the phosphites (I) are formulated.

Examples of the phenol antioxidant include the following.

(1) Examples of alkylated monophenol 2,6-di-t-butyl-4-methylphenol, 2,4,6-tri-t-butylphenol, 2,6-di-t-butyl-4-butylphenol, 2-t-butyl-4,6-dimethylphenol, 2,6-di-t-butyl-4-ethylphenol, 2,6-di-t-butyl-4-n-butylphenol, 2,6-di-t-butyl-4-isobutylphenol, 2,6-dicyclopentyl-4-methylphenol, 2-(α-methylcyclohexyl)-4, 6-dimethylphenol, 2,6-dioctadecyl-4-methylphenol, 2,4,6-tricyclohexylphenol, 2,6-di-t-butyl-4-methoxymethylphenol, 2,6-di-nonyl-4-methylphenol, 2,4-dimethyl-6-(1'-methylundecyl-1'-yl)phenol, 2,4-dimethyl-6'-(1'-methylheptadecyl-1'-yl)phenol, 2,4-dimethyl-6-(1'-methyltridecyl-1'-yl)phenol and a mixture thereof.

(2) Examples of alkylthiomethylphenol 2,4-dioctylthiomethyl-6-t-butylphenol, 2,4-dioctylthiomethyl-6-methylphenol, 2,4-dioctylthiomethyl-6-ethylphenol, 2,6-didodecylthiomethyl-4-nonylphenol and a mixture thereof.

(3) Examples of hydroquinone and alkylated hydroquinone 2,6-di-t-butyl-4-methoxyphenol, 2,5-di-t-butylhydroquinone, 2,5-di-t-amylhydroquinone, 2,6-diphenyl-4-octadecyloxyphenol, 2,6-di-t-butylhydroquinone, 2,5-di-t-butyl-4-hydroxyanisole, 3,5-di-t-butyl-4-hydroxyphenyl stearate, bis(3,5-di-t-butyl-4-hydroxyphenyl)adipate and a mixture thereof.

(4) Examples of tocopherol

α-tocopherol, β-tocopherol, γ-tocopherol, δ-tocopherol and a mixture thereof.

(5) Examples of hydroxylated thiodiphenyl ether 2,2'-thiobis(6-t-butylphenol), 2,2'-thiobis(4-methyl-6-t-butylphenol), 2,2'-thiobis(4-octylphenol), 4,4'-thiobis(3-methyl-6-t-butylphenol), 4,4'-thiobis(2-methyl-6-t-butylphenol), 4,4'-thiobis(3,6-di-t-amylphenol), 4,4'-(2,6-dimethyl-4-hydroxyphenyl)disulfide and the like (6) Examples of alkylidenebisphenol and derivative thereof.

2,2'-methylenebis(4-methyl-6-t-butylphenol), 2,2'-methylenebis(4-ethyl-6-t-butylphenol), 2,2'-methylenebis[4-methyl-6-(α-methylcyclohexyl)phenol], 2,2'-methylenebis(4-methyl-6-cyclohexylphenol), 2,2'-methylenebis(4-methyl-6-nonylphenol), 2,2'-methylenebis(4,6-di-t-butylphenol), 2,2'-ethylidenebis(4,6-di-t-butylphenol), 2,2'-ethylidenebis(4-isobutyl-6-t-butylphenol), 2,2'-methylenebis[6-(α-methylbenzyl)-4-nonylphenol], 2,2'-methylenebis[6-(α,α-dimethylbenzyl)-4-nonylphenol)], 4,4'-methylenebis(6-t-butyl-2-methylphenol), 4,4'-methylenebis(2,6-di-t-butylphenol), 4,4'-butylidenebis(3-methyl-6-t-butylphenol), 1,1-bis(4-hydroxyphenyl)cyclohexane, 1,1-bis(5-t-butyl-4-hydroxy-2-methylphenyl)butane, 2,6-bis(3-t-butyl-5-methyl-2-hydroxybenzyl)-4-methylphenol, 1,1,3-tris(5-t-butyl-4-hydroxy-2-methylphenyl)butane, 1,1-bis(5-t-butyl-4-hydroxy-2-methylphenyl)-3-n-dodecylmercaptobutane, bis[3,3-bis(3'-t-butyl-4'-hydroxyphenyl)butyrate], bis[2-(3'-t-butyl-2'-hydroxy-5'-methylbenzyl)-6-t-butyl-4-methylphenyl]terephthalate, 1,1-bis(3,5-dimethyl-2-hydroxyphenyl)butane, 2,2-bis(3,5-di-t-butyl-4-hydroxyphenyl)propane, 2,2-bis(5-t-butyl-4-hydroxy-2-methylphenyl)-4-n-dodecylmercaptobutane, 1,1,5,5-tetra(5-t-butyl-4-hydroxy-2-methylphenyl)pentane, 2-t-butyl-6-(3'-t-butyl-5'-methyl-2'-hydroxybenzyl)-4-methylphenyl acrylate, 2,4-di-t-pentyl-6-[1-(2-hydroxy-3,5-di-t-pentylphenyl)ethyl]phenyl acrylate and a mixture thereof.

(7) Examples of O—, N— and S-benzyl derivative 3,5,3',5'-tetra-t-butyl-4,4'-dihydroxydibenzyl ether, octadodecyl-4-hydroxy-3,5-dimethylbenzylmercapto acetate, tris(3,5-di-t-butyl-4-hydroxybenzyl)amine, bis(4-t-butyl-3-hydroxy-2,6-dimethylbenzyl)dithioterephthalate, bis(3,5-di-t-butyl-4-hydroxybenzyl)sulfide, isooctyl-3,5-di-t-butyl-4-hydroxybenzylmercapto acetate and a mixture thereof.

(8) Examples of hydroxybenzylated malonate derivative dioctadecyl-2,2-bis(3,5-di-t-butyl-2-hydroxybenzyl) malonate, dioctadecyl-2-(3-t-butyl-4-hydroxy-5-methylbenzyl)malonate, didodecylmercaptoethyl-2,2-bis(3, 5-di-t-butyl-4-hydroxybenzyl)malonate, bis[4-(1,1,3,3-tetramethylbutyl)phenyl]-2,2-bis(3,5-di-t-butyl-4-hydroxybenzyl)malonate and a mixture thereof.

(9) Examples of aromatic hydroxybenzyl derivative 1,3,5-trimethyl-2,4,6-tris(3,5-di-t-butyl-4-hydroxybenzyl)benzene, 1,4-bis(3,5-di-t-butyl-4-hydroxybenzyl)-2,3,5,6-tetramethylbenzene, 2,4,6-tris(3,5-t-butyl-4-hydroxybenzyl)phenol and a mixture thereof.

(10) Examples of triazine derivative 2,4-bis(n-octylthio)-6-(4-hydroxy-3,5-di-t-butylanilino)-1,3,5-triazine, 2-n-octylthio-4,6-bis(4-hydroxy-3,5-di-t-butylanilino)-1,3,5-triazine, 2-n-octylthio-4,6-bis(4-hydroxy-3,5-di-t-butylphenoxy)-1,3,5-triazine, 2,4,6-tris(3, 5-di-t-butyl-4-hydroxy)-1,3,5-triazine, tris(4-t-butyl-3-hydroxy-2,6-dimethylbenzyl isocyanurate, tris(3,5-di-t-butyl-4-hydroxybenzyl)isocyanurate, 2,4,6-tris(3,5-di-t-butyl-4-hydroxyphenylethyl)-1,3,5-triazine, 2,4,6-tris(3,5-di-t-butyl-4-hydroxyphenylpropyl)-1,3,5-triazine, tris(3,5-dicyclohexyl-4-hydroxybenzyl)isocyanurate, tris[2-(3',5'-di-t-butyl-4'-hydroxycinnamoyloxy)ethyl]isocyanurate and a mixture thereof.

(11) Examples of benzyl phosphonate derivative dimethyl-3,5-di-t-butyl-4-hydroxybenzyl phosphonate, diethyl-3,5-di-t-butyl-4-hydroxybenzyl phosphonate, dioctadecyl-3,5-di-t-butyl-4-hydroxybenzyl phosphonate, dioctadecyl-5-t-butyl-4-hydroxy-3-methylbenzyl phosphonate, calcium salt of 3,5-di-t-butyl-4-hydroxybenzyl phosphonic acid monoester and a mixture thereof.

(12) Examples of acylaminophenol derivative anilide 4-hydroxylaurate, anilide 4-hydroxystearate, octyl-N-(3,5-di-t-butyl-4-hydroxyphenyl)carbamate and a mixture thereof.

(13) Ester of β-(3,5-di-t-butyl-4-hydroxyphenyl) propionic acid and the following monohydric or polyhydric alcohol:

methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2,2,2]octane and a mixture thereof.

(14) Ester of β-(5-t-butyl-4-hydroxy-3-methylphenyl) propionic acid and the following monohydric or polyhydric alcohol:

methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2,2,2]octane and a mixture thereof

(15) Ester of β-(3,5-dicyclohexyl-4-hydroxyphenyl) propionic acid and the following monohydric or polyhydric alcohol:

methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2,2,2]octane and a mixture thereof

(16) Ester of 3,5-t-butyl-4-hydroxyphenylacetic acid and the following monohydric or polyhydric alcohol:

methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2,2,2]octane and a mixture thereof

(17) Examples of amide of β-(3,5-di-t-butyl-4-hydroxyphenyl)propionic acid

N,N'-bis[3-(3',5'-di-t-butyl-4'-hydroxyphenyl)propionyl] hydrazine, N,N'-bis[3-(3',5'-di-t-butyl-4'-hydroxyphenyl) propionyl]hexamethylenediamine, N,N'-bis[3-(3',5'-di-t-butyl-4'-hydroxyphenyl)propionyl]trimethylenediamine and a mixture thereof.

Examples of the sulfur antioxidant include:

dilauryl 3,3'-thiodipropionate, tridecyl 3,3'-thiodipropionate, dimyristyl 3,3'-thiodipropionate, distearyl 3,3'-thiodipropionate, lauryl stearyl 3,3'-thiodipropionate, neopentanetetrayltetrakis(3-lauryl thiopropionate) and the like.

Examples of the phosphorous antioxidant include the following:

triphenyl phosphite, tris(nonylphenyl)phosphite, tris(2,4-di-t-butylphenyl)phosphite, trilauryl phosphite, trioctadecyl phosphite, distearyl pentaerythritol diphosphite, diisodecyl pentaerythritol diphosphite, bis(2,4-di-t-butylphenyl) pentaerythritol diphosphite, bis(2,4-di-t-butyl-6-methylphenyl)pentaerythritol diphosphite, bis(2,4-di-t-butyl-6-methylphenyl)pentaerythritol diphosphite, bis(2,6-di-t-butyl-4-methylphenyl)pentaerythritol diphosphite, bis(2,4,6-tri-t-butylphenyl)pentaerythritol diphosphite, tristearyl sorbitol triphosphite, tetrakis(2,4-di-t-butylphenyl)-4,4'-diphenylene diphosphite, 2,2'-methylenebis(4,6-di-t-butylphenyl)2-ethylhexyl phosphite, 2,2'-ethylidenebis(4,6-di-t-butylphenyl)fluoro phosphite, bis(2,4-di-t-butyl-6-methylphenyl)ethyl phosphite, bis(2,4-di-t-butyl-6-methylphenyl)methyl phosphite, (2,4,6-tri-t-butylphenyl)-5-ethyl-5-butyl-1,3,2-oxaphosphorinane, 2,2',2"-nitrilo[triethyltris(3,3',5,5'-tetra-t-butyl-1,1'-biphenyl-2,2'-diyl) phosphite and a mixture thereof Examples of the ultraviolet absorber include the following:

(1) Examples of salicylate derivative phenyl salicylate, 4-t-butylphenyl salicylate, 2,4-di-t-butylphenyl 3',5'-di-t-butyl-4'-hydroxybenzoate, 4-t-octylphenyl salicylate, bis(4-t-butylbenzoyl)resorcinol, benzoylresorcinol, hexadecyl 3',5'-di-t-butyl-4'-hydroxybenzoate, octadecyl 3',5'-di-t-butyl-4'-hydroxybenzoate, 2-methyl-4,6-di-t-butylphenyl 3',5'-di-t-butyl-4'-hydroxybenzoate and a mixture thereof.

(2) Examples of 2-hydroxybenzophenone derivative 2,4-dihydroxybenzophenone, 2-hydroxy-4-methoxybenzophenone, 2-hydroxy-4-octoxybenzophenone, 2,2'-dihydroxy-4-methoxybenzophenone, bis(5-benzoyl-4-hydroxy-2-methoxyphenyl)methane, 2,2',4,4'-tetrahydroxybenzophenone and a mixture thereof.

(3) Examples of 2-(2'-hydroxyphenyl)benzotriazole 2-(2-hydroxy-5-methylphenyl)benzotriazole, 2-(3',5'-di-t-butyl-2'-hydroxyphenyl)benzotriazole, 2-(5'-t-butyl-2'-hydroxyphenyl)benzotriazole, 2-(2'-hydroxy-5'-t-octylphenyl)benzotriazole, 2-(3-t-butyl-2-hydroxy-5-methylphenyl)-5-chlorobenzotriazole, 2-(3'-s-butyl-2'-hydroxy-5'-t-butylphenyl)benzotriazole, 2-(2'-hydroxy-4'-octyloxypheny)benzotriazole, 2-(3',5'-di-t-amyl-2'-hydroxyphenyl)benzotriazole, 2-[2'-hydroxy-3',5'-bis(α,α-dimethylbenzyl)phenyl]-2H-benzotriazole, 2-[(3'-t-butyl-2'-hydroxyphenyl)-5'-(2-octyloxycarbonylethyl)phenyl]-5-chlorobenzotriazole, 2-[3'-t-butyl-5'-[2-(2-ethylhexyloxy) carbonylethyl]-2'-hydroxyphenyl]-5-chlorobenzotriazole, 2-[3'-t-butyl-2'-hydroxy-5'-(2-methoxycarbonylethyl) phenyl]-5-chlorobenzotriazole, 2-[3'-t-butyl-2'-hydroxy-5'-(2-methoxycarbonylethyl)phenyl]benzotriazole, 2-[3'-t-butyl-2'-hydroxy-5-(2-octyloxycarbonylethyl)phenyl] benzotriazole, 2-[3'-t-butyl-2'-hydroxy-5'-[2-(2-ethylhexyloxy)carbonylethyl]phenyl]benzotriazole, 2-[2-hydroxy-3-(3,4,5,6-tetrahydrophthalimidemethyl)-5-methylphenyl]benzotriazole, 2-(3',5'-di-t-butyl-2-hydroxyphenyl)-5-chlorobenzotriazole, mixture of 2-(3'-dodecyl-2'-hydroxy-5'-methylphenyl)benzotriazole and 2-[3'-t-butyl-2'-hydroxy-5'-(2-isooctyloxycarbonylethyl) phenyl]benzotriazole, 2,2'-methylenebis[6-(2H-benzotriazol-2-yl)-4-(1,1,3,3-tetramethylbutyl)phenol, 2,2'-methylenebis[4-t-butyl-6-(2H-benzotriazol-2-yl)phenol, condensate of poly(3-11)(ethylene glycol) and 2-[3'-t-butyl-2'-hydroxy-5'-(2-methoxycarbonylethyl)phenyl] benzotriazole, condensate of poly(3-11)(ethylene glycol) and methyl 3-[3-(2H-benzotriazol-2-yl)-5-t-butyl-4-hydroxyphenyl]propionate, 2-ethylhexyl 3-[3-t-butyl-5-(5-chloro-2H-benzotriazol-2-yl)-4-hydroxyphenyl]propionate, octyl 3-[3-t-butyl-5-(5-chloro-2H-benzotriazol-2-yl)-4-hydroxyphenyl]propionate, methyl 3-[3-t-butyl-5-(5-chloro-2H-benzotriazol-2-yl)-4-hydroxyphenyl]propionate, 3-[3-t-butyl-5-(5-chloro-2H-benzotriazol-2-yl)-4-hydroxyphenyl] propionic acid and a mixture thereof.

Examples of the photostabilizer include the following.

(1) Examples of hindered amine photostabilizer bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(N-octoxy-2,2,6,6-tetramethyl-4-piperidyl)sebacate, bis(N-benzyloxy-2,2,6,6-tetramethyl-4-piperidyl)sebacate, bis(N-cyclohexyloxy-2,2,6,6-tetramethyl-4-piperidyl)sebacate, bis(1,2,2,6,6-pentamethyl-4-piperidyl) 2-(3,5-di-t-butyl-4-hydroxybenzyl)-2-butylmalonate, bis(1-acrolyl-2,2,6,6-tetramethyl-4-piperidyl) 2,2-bis(3,5-di-t-butyl-4-hydroxybenzyl)-2-butylmalonate, bis(1,2,2,6,6-penatmethyl-4-piperidyl decanedioate, 2,2,6,6-tetramethyl-4-piperidyl methacrylate, 4-[3-(3,5-di-t-butyl-4-hydroxyphenyl)propionyloxy]-1-[2-(3-(3,5-di-t-butyl-4-hydroxyphenyl)propionyloxy)ethyl]-2,2,6,6-tetramethylpiperidine, 2-methyl-2-(2,2,6,6-tetramethyl-4-piperidyl)amino-N-(2,2,6,6-tetramethyl-4-piperidyl) propionamide, tetrakis(2,2,6,6-tetramethyl-4-piperidyl) 1,2, 3,4-butanetetracarboxylate, tetrakis(1,2,2,6,6-pentamethyl-4-piperidyl) 1,2,3,4-butanetetracarboxylate, mixed esterified product of 1,2,3,4-butanetetracarboxylic acid and 1,2,2,6,6-pentamethyl-4-piperidinol and 1-tridecanol, mixed esterified product of 1,2,3,4-butanetetracarboxylic acid and 2,2,6,6-tetramethyl-4-piperidinol and 1-tridecanol, mixed esterified product of 1,2,3,4-butanetetracarboxylic acid and 1,2,2,6,6-pentamethyl-4-piperidinol and 3,9-bis(2-hydroxy-1,1-dimethylethyl)-2,4,8,10-tetraoxaspiro[5.5]undecane, mixed esterified product of 1,2,3,4-butanetetracarboxylic acid and 2,2,6,6-tetramethyl-4-piperidinol and 3,9-bis(2-hydroxy-1,1-dimethylethyl)-2,4,8,10-tetraoxaspiro[5.5]undecane, polycondensate of dimethyl succinate and 1-(2-hydroxyethyl)-4-hydroxy-2,2,6,6-tetramethylpiperidine, poly[(6-morpholino-1,3,5-triazin-2,4-diyl)((2,2,6,6-tetramethyl-4-piperidyl)imino)hexamethylene ((2,2,6,6-tetramethyl-4-piperidyl)imino)], poly[(6-(1,1,3,3-tetramethylbutyl)imino-1,3,5-triazin-2,4-diyl) ((2,2,6,6-tetramethyl-4-piperidyl)imino)hexamethylene ((2,2,6,6-tetramethyl-4-piperidyl)imino)], polycondensate of N,N'-bis (2,2,6,6-tetramethyl-4-piperidyl)hexamethylenediamine and 1,2-bromoethane, N,N',4,7-tetrakis[4,6-bis(N-butyl-N-(2,2,6,6-tetramethyl-4-piperidyl)amino)-1,3,5-triazin-2-yl]-4,7-diazadecane-1,10 diamine, N,N',4-tris[4,6-bis(N-butyl-N-(2,2,6,6-tetramethyl-4-piperidyl)amino)-1,3,5-triazin-2-yl]-4,7-diazadecane-1,10 diamine, N,N',4,7-tetrakis[4,6-bis(N-butyl-N-(1,2,2,6,6-pentamethyl-4-piperidyl)amino)-1,3,5-triazin-2-yl]-4,7-diazadecane-1,10 diamine, N,N',4-tris[4,6-bis(N-butyl-N-(1,2,2,6,6-pentamethyl-4-piperidyl)amino)-1,3,5-triazin-2-yl]-4,7-diazadecane-1,10 diamine and a mixture thereof.

(2) Examples of acrylate photostabilizer ethyl α-cyano-β,β-diphenylacrylate, isooctyl α-cyano-β,β-diphenylacrylate, methyl α-carbomethoxycinnamate, methyl α-cyano-β-methyl-methoxycinnamate, butyl α-cyano-β-methyl-p-methoxycinnamate, methyl α-carbomethoxy-p-methoxycinnamate and N-(β-carbomethoxy-β-cyano-vinyl-)-2-methylindoline and a mixture thereof.

(3) Examples of nickel photostabilizer nickel complex of 2,2'-thiobis-[4-(1,1,3,3-tetramethylbutyl)phenol], nickel dibutyldithiocarbamate, nickel salt of monoalkyl ester, nickel complex of ketoxime and a mixture thereof.

(4) Examples of oxamide photostabilizer 4,4'-dioctyloxyoxanilide, 2,2'-diethoxyoxanilide, 2,2'-dioctyloxy-5,5'-di-t-butylanilide, 2,2'-didodecyloxy-5,5'-di-t-butylanilide, 2-ethoxy-2'-ethyloxanilide, N,N'-bis(3-dimethylaminopropyl)oxamide, 2-ethoxy-5-t-butyl-2'-ethoxyanilide, 2-ethoxy-5,4'-di-t-butyl-2'-ethyloxanilide and a mixture thereof (5) Examples of 2-(2-hydroxyphenyl)-1,3,5-triazine photostabilizer 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(4-methylphenyl)-1,3,5-triazine, 2-[2-hydroxy-4-(2-hydroxy-3-butyloxypropoxy)phenyl]-4,6-bis(2,4-dimethylphenyl)-1,3,5-triazine, 2-[2-hydroxy-4-(2-hydroxy-3-octyloxyphenyl)-4,6-bis(2,4-dimethylphenyl)-1,3,5-triazine and a mixture thereof.

Examples of the metal inactivating agent include the following:

N,N'-diphenyloxamide, N-salicylal-N'-salicyloylhydrazine, N,N'-bis(salicyloyl)hydrazine, N,N'-bis (3,5-di-t-butyl-4-hydroxyphenylpropionyl)hydrazine, 3-salicyloylamino-1,2,4-triazole, bis(benzylidene)oxalyl dihydrazide, oxalinide, isophthaloyl dihydrazide, sebacoyl-bisphenyl hydrazide, N,N'-bis(salicyloyl)thiopropionyl dihydrazide and a mixture thereof.

Examples of the peroxide scavenger include ester of β-thiodipropionic acid, mercaptobenzoimidazole, zinc salt of 2-mercaptobenzoimidazole, zinc salt of dibutyldithiocarbamic acid, dioctadecyl disulfide, pentaerythritol tetrakis(β-dodecylmercapto)propionate and a mixture thereof.

Examples of the polyamide stabilizer include copper or divalent manganese salt of iodide or phosphorous compound and a mixture thereof.

Examples of the hydroxyamine include N,N-dibenzylhydroxyamine, N,N-diethylhydroxyamine, N,N-dioctylhydroxyamine, N,N-dilaurylhydroxyamine, N,N-ditetradecylhydroxyamine, N,N-dihexadecylhydroxyamine, N,N-dioctadecylhydroxyamine, N,N-dibenzylhydroxyamine, N,N-dibenzylhydroxyamine, N-hexadecyl-N-octadecylhydroxyamine, N-heptadecyl-N-octadecylhydroxyamine and a mixture thereof.

Examples of the neutralizing agent include calcium stearate, zinc stearate, magnesium stearate, hydrotalcite (basic magnesium aluminum hydroxycarbonate hydride), melamine, amine, polyamide, polyurethane and a mixture thereof.

Examples of the lubricant include aliphatic hydrocarbon (e.g. paraffin, wax, etc.), higher aliphatic acid having 8 to 22 carbon atoms, higher aliphatic acid (having 8 to 22 carbon atoms) metal (e.g. Al, Ca, Mg, Zn) salt, aliphatic alcohol having 8 to 22 carbon atoms, polyglycol, ester of higher fatty acid having 4 to 22 carbon atoms and aliphatic monohydric alcohol having 4 to 18 carbon atoms, higher aliphatic amide having 8 to 22 carbon atoms, silicone oil, rosin derivative and the like.

Examples of the nucleating agent include the following:
sodium 2,2'-methylenebis(4,6-di-t-butylphenyl) phosphate, [phosphoric acid-2,2'-methylenebis(4,6-di-t-butylphenyl)]dihydroxyaluminum, bis[phosphoric acid-2,2'-methylenebis(4,6-di-t-butylphenyl)]dihydroxyaluminum, tris[phosphoric acid-2,2'-methylenebis(4,6-di-t-butylphenyl)]aluminum, sodium bis(4,6-di-t-butylphenyl) phosphate, benzoic acid metal salt such as sodium benzoate, aluminum p-t-butylbenzoate, 1,3:2,4-bis(O-benzylidene) sorbitol, 1,3:2,4-bis(O-ethylbenzylidene)sorbitol, 1,3:2,4-bis(O-methylbenzylidene)sorbitol, 1,3-O-3,4-dimethylbenzylidene-2,4-O-benzylidenesorbitol, 1,3-O-benzylidene-2,4-O-3,4-dimethylbenzylidene sorbitol, 1,3:2,4-bis(O-3,4-dimethylbenzylidene)sorbitol, 1,3-O-p-chlorobenzylidene-2,4-O-3,4-dimethylbenzylidene sorbitol, 1,3-O-3,4-dimethylbenzylidene-2,4-O-p-chlorobenzylidene sorbitol, 1,3:2,4-bis(O-p-chlorobenzylidene)sorbitol and a mixture thereof.

Examples of the filler include calcium carbonate, silicate, glass fiber, asbestos, talc, kaolin, mica, barium sulfate, carbon black, carbon fiber, zeolite and a mixture thereof.

Among these additives above, phenol antioxidant, phosphorous antioxidant, ultraviolet absorber, hindered amine photostabilizer, peroxide scavenger and neutralizing agent are preferably used.

Examples of the particularly preferred phenol antioxidant include the following compounds, and they may be used in combination of the two or more:

2,6-di-t-butyl-4-methylphenol, 2,4,6-tri-t-butylphenol, 2,4-dioctylthiomethyl-6-methylphenol, 2,2'-thiobis(6-t-butylphenol), 4,4'-thiobis(3-methyl-6-t-butylphenol), 2,2'-methylenebis(4-methyl-6-t-butylphenol), 2,2'-methylenebis(4-ethyl-6-t-butylphenol), 2,2'-methylenebis[4-ethyl-6-(α-methylcyclohexyl)phenol], 2,2'-methylenebis(4-methyl-6-cyclohexylphenol), 2,2'-methylenebis(4,6-di-t-butylphenol), 2,2'-ethylidenebis(4,6-di-t-butylphenol), 4,4'-methylenebis(6-t-butyl-2-methylphenol), 4,4'-methylenebis(2,6-di-t-butylphenol), 4,4'-butylidenebis(3-methyl-6-t-butylphenol), 1,1'-bis(4-hydroxyphenyl)cyclohexane, 1,1-bis(5-t-butyl-4-hydroxy-2-methylphenyl)butane, 1,1,3-tris(5-t-butyl-4-hydroxy-2-methylphenyl)butane, ethylene glycol, bis[3,3-bis-(3'-t-butyl-4'-hydroxyphenyl)butyrate], 2-t-butyl-6-(3'-t-butyl-5'-methyl-2'-hydroxybenzyl)-4-methylphenyl acrylate, 2,4-di-t-pentyl-6-[1-(2-hydroxy-3,5-di-t-pentylphenyl)ethyl]phenyl acrylate, 2,4,6-tris(3,5-di-t-butyl-4-phenoxy)-1,3,5-triazine, tris(4-t-butyl-3-hydroxy-2,6-dimethylbenzyl)isocyanurate, tris(3,5-di-t-butyl-4-hydroxybenzyl)isocyanurate, tris[2-(3',5'-di-t-butyl-4'-hydroxycinnamoyloxy)ethyl]isocyanurate, diethyl-3,5-di-t-butyl-4-hydroxybenzyl phosphonate, di-n-octadecyl-3,5-di-t-butyl-4-hydroxybenzyl phosphonate, calcium salt of 3,5-di-t-butyl-4-hydroxybenzylphosphonic acid monoester, n-octadecyl 3-(3,5-di-t-butyl-4-hydroxyphenyl)propionate, neopentanetetrayltetrakis(3,5-di-t-butyl-4-hydroxycinnamate), thiodiethylenebis(3,5-di-t-butyl-4-hydroxycinnamate), 1,3,5-trimethyl-2,4,6-tris(3,5-di-t-butyl-4-hydroxybenzyl)benzene, 3,6-dioxaoctamethylenebis(3,5-di-t-butyl-4-hydroxycinnamate), hexamethylenebis(3,5-di-t-butyl-4-hydroxycinnamate), triethylene glycol bis(5-t-butyl-4-hydroxy-3-methylcinnamate), 3,9-bis[2-(3-(3-t-butyl-4-hydroxy-5-methylphenyl)propionyloxy)-1-dimethylethyl]-2,4,8,10-tetraoxaspiro [5.5]undecane, N,N'-bis[3-(3',5'-di-t-butyl-4'-hydroxyphenyl)propionyl]hydrazine, N,N'-bis[3-(3',5'-di-t-butyl-4'-hydroxyphenyl)propionyl]hexamethylenediamine and the like.

Examples of the particularly preferred phosphorous antioxidant include the following, and they may be used in combination of the two or more:

tris(nonylphenyl)phosphite, tris(2,4-di-t-butylphenyl)phosphite, distearyl pentaerythritol diphosphite, bis(2,4-di-t-butylphenyl)pentaerythritol diphosphite, bis(2,4-di-t-butyl-6-methylphenyl)pentaerythritol diphosphite, bis(2,6-di-t-butyl-4-methylphenyl)pentaerythritol diphosphite, tetrakis(2,4-di-t-butylphenyl)-4,4'-diphenylenediphosphite, 2,2'-methylenebis(4,6-di-t-butylphenyl) 2-ethylhexyl phosphite, 2,2'-ethylidenebis(4,6-di-t-butylphenyl) fluorophosphite, bis(2,4-di-t-butyl-6-methylphenyl) ethylphosphite, 2-(2,4,6-tri-t-butylphenyl)-5-ethyl-5-butyl-1,3,2-oxaphospholinane, 2,2',2"-nitrilo[triethyl-tris(3,3',5,5'-tetra-t-butyl-1,1'-biphenyl-2,2'-diyl)phosphite and the like Examples of the particularly preferred ultraviolet absorber include the following, and two or more kinds of them can be used.

phenyl salicylate, 4-t-butylphenyl salicylate, 2,4-di-t-butylphenyl 3',5'-di-t-butyl-4'-hydroxybenzoate, 4-t-octylphenyl salicylate, 2,4-dihydroxybenzophenone, 2-hydroxy-4-methoxybenzophenone, 2-hydroxy-4-octoxybenzophenone, 2,2'-dihydroxy-4-methoxybenzophenone, bis(5-benzoyl-4-hydroxy-2-methoxyphenyl)methane, 2,2',4,4'-tetrahydroxybenzophenone, 2-(2-hydroxy-5-methylphenyl)benzotriazole, 2-(3',5'-di-t-butyl-2'-hydroxyphenyl)benzotriazole, 2-(5'-t-butyl-2'-hydroxyphenyl)benzotriazole, 2-(2'-hydroxy-5'-t-octylphenyl)benzotriazole, 2-(3-t-butyl-2-hydroxy-5-methylphenyl)-5-chlorobenzotriazole, 2-(3'-s-butyl-2'-hydroxy-5'-t-butylphenyl)benzotriazole, 2-(2'-hydroxy-4'-octyloxyphenyl)benzotriazole, 2-(3',5'-di-t-amyl-2'-hydroxyphenyl)benzotriazole, 2-[2'-hydroxy-3',5'-bis(α,α-dimethylbenzyl)phenyl]-2H-benzotriazole and the like Examples of the particularly preferred photostabilizer include the following, and two or more kinds of them can be used.

bis(2,2,6,6-tetramethyl-4-piperidyl)sebacate, bis(1,2,2,6,6-pentamethyl-4-piperidyl)sebacate, bis(N-octoxy-2,2,6,6-pentamethyl-4-piperidyl)sebacate, bis(N-octoxy-2,2,6,6-pentamethyl-4-piperidyl)sebacate, bis(N-benzyloxy-2,2,6,6-tetramethyl-4-piperidyl)sebacate, bis(N-cyclohexyloxy-2,2,6,6-tetramethyl-4-piperidyl)sebacate, bis(1,2,2,6,6-pentamethyl-4-piperidyl) 2-(3,5-di-t-butyl-4-hydroxybenzyl)-2-butylmalonate, bis(1-acryloyl-2,2,6,6-tetramethyl-4-piperidyl) 2,2-bis(3,5-di-t-butyl-4-hydroxybenzyl)-2-butylmalonate, bis(2,2,6,6-tetramethyl-4-piperidyl)succinate, 2,2,6,6-tetramethyl-4-piperidyl methacrylate, 4-[3-(3,5-di-t-butyl-4-hydroxyphenyl) propionyloxy]-1-[2-(3-(3,5-di-t-butyl-4-hydroxyphenyl) propionyloxy)ethyl]-2,2,6,6-tetramethylpiperidine, 2-methyl-2-(2,2,6,6-tetramethyl-4-piperidyl)amino-N-(2,2,6,6-tetramethyl-4-piperidyl)propionamide, tetrakis(2,2,6,6-tetramethyl-4-piperidyl) 1,2,3,4-butanetetracarboxylate. tetrakis(1,2,6,6-pentamethyl-4-piperidyl) 1,2,3,4-butanetetracarboxylate, mixed esterified product of 1,2,3,4-butanetetracarboxylic acid and 1,2,2,6,6-pentamethyl-4-piperidinol and 1-tridecanol, mixed esterified product of 1,2,3,4-butanetetracarboxylic acid and 2,2,6,6-tetramethyl-4-piperidinol and 1-tridecanol, mixed esterified product of 1,2,3,4-tetracarboxylic acid and 1,2,2,6,6-pentamethyl-4-piperidinol and 3,9-bis(2-hydroxy-1,1-dimethylethyl)-2,4,8,10-tetraoxaspiro[5.5]undecane, mixed esterified product of 1,2,3,4-butanetetracarboxylic acid and 2,2,6,6-tetramethyl-4-piperidinol and 3,9-bis(2-hydroxy-1,1-dimethylethyl)-2,4,8,10-tetraoxaspiro[5.5]undecane, polycondensate of dimethyl succinate and 1-(2-hydroxyethyl)-4-hydroxy-2,2,6,6-tetramethylpiperidine, poly[(6-morpholino-1,3,5-triazin-2,4-diyl)((2,2,6,6-tetramethyl-4-piperidyl)imino) hexamethylene ((2,2,6,6-tetramethyl-4-piperidyl)imino)], poly[(6-(1,1,3,3-tetramethylbutyl)imino-1,3,5-triazin-2,4-diyl) ((2,2,6,6-tetramethyl-4-piperidyl)imino) hexamethylene ((2,2,6,6-tetramethyl-4-piperidyl)imino)] and the like When the phosphites (I) and optionally used other additives are formulated in the organic material, known any methods and devices for obtaining a homogeneous mixture can be used. For example, when the organic material is a solid polymer, the phosphites (I) and other additives can be directly dry-blended in the solid polymer, and the phosphite compound or other additives can also be formulated in the solid polymer in the form of a master batch. When the organic material is a liquid polymer, the phosphites (I) and other additives can be formulated in the polymer solution during or immediately after polymerization in the form of a solution or a dispersion. On the other hand, when the organic material is a liquid such as oil, the phosphites (I) and other additives can also be dissolved by direct addition, and the phosphites (I) and other additives can also be added in the form of being dissolved or dispersed in the liquid medium.

The phosphites (I) of the present invention have excellent performance as a stabilizer for various organic materials such as thermoplastic resin (e.g. polyolefin, etc.), and organic materials containing this compound are stable to heat and oxidation during their production, processing and use, which results in high-quality product.

The following Examples further illustrate the present invention in detail but are not to be construed to limit the scope thereof.

EXAMPLE 1

Production of 6-[2-(3,5-di-t-butyl-4-hydroxyphenylmethoxy)ethoxy]4,8-di-t-butyl-2,10-dimethyl-12H-dibenzo[d,g][1,3,2]dioxaphosphosine (compound 1)

In a flask equipped with a thermometer, a stirrer and a condenser, 8.5 g of 2,2'-methylenebis(6-t-butyl-4-methylphnenol) and 100 ml of toluene were charged under a nitrogen gas flow. After adding 3.4 g of phosphorous trichloride with stirring, 5.6 g of triethylamine was added, and the mixture was maintained at 80° C. for 7 hours.

After cooling to room temperature, 50 ml of toluene and 7.0 g of 2-(3,5-di-t-butyl-4-hydroxyphenylmethyloxy) ethanol were added. Thereafter, 2.8 g of triethylamine was added to the mixture and then the mixture was maintained at 80° C. for 8 hours.

After cooling to room temperature, the formed hydrochloride of triethylamine was filtered. The filtrate was concentrated and the residue was treated by silica gel chromatography to obtain 11.2 g of a white crystaline compound.

Mass spectrometric analysis (FD-MS): m/z 648

Melting point: 169° C.

$^1$H-NMR (CDCl$_3$)

1.38 (s, 18H), 1.44 (s, 18H), 2.28 (s, 6H), 3.35 (d, 1H), 3.38 (t, 2H), 4.29 (d, 1H), 4.56 (s, 2H), 4.62 (m, 2H), 5.19 (s, 2H), 7.02 (d, 2H), 7.09 (d, 2H), 7.19 (s, 2H)

$^{31}$P-NMR (CDCl$_3$) 129 ppm

EXAMPLE 2

Production of 6-[2-(3,5-di-t-butyl-4-hydroxyphenylmethoxy)ethoxy]4,8,10-tetra-t-pentyl-12-methyl-12H-dibenzo[d,g][1,3,2] dioxaphosphosine (compound 2)

According to the same manner as that described in Example 1 except for using 12.4 g of 2,2'-ethylidenebis(4,6-di-t-pentylphenol), in place of 2,2'-methylenebis(6-t-butyl-4-methylphenol), 11 g of a white crystaline compound was obtained.

Mass spectrometric analysis (FD-MS): m/z 802

Melting point: 97° C.

$^1$H-NMR (CDCl$_3$)

0.62(m, 12H), 1.23–1.45 (m, 42H), 1.56(m, 3H), 1.78 (m, 8H), 3.83 (m, 2H), 4.54 (S, 2H), 4.61 (m, 2H), 4.87 (q, 1H), 5.19 (s, 1H), 7.07 (d, 2H), 7.19 (s, 2H), 7.30 (s, 2H)

$^{31}$P-NMR (CDCl3) 127 ppm

EXAMPLE 3

Thermal stability test of polypropylene

| [Formulation] | |
|---|---|
| Polypropylene (block) | 100 Parts by weight |
| Calcium stearate | 0.05 Parts by weight |
| Compound to be tested | 0.05 Parts by weight |

C-1: Compound 1 (produced in Example 1)
C-2: Compound 2 (produced in Example 2)

P-1: 2,10-dimethyl-4,8-di-t-butyl-6-{2-[3-(3-t-butyl-4-hydroxy-5-methylphenyl)propionyloxy]ethoxy}-12H-dibenzo[d,g][1,3,2]dioxaphosphosine Using a 30 mm φ sigle-screw extruder, the above formulation was repelletized at 250° C. MFR (g/10 minutes) of the resulting pellets was measured at 250° C. under a load of 2160 g for a detention time of 5 minutes by using a melt indexer. The results are shown in Table 1. The smaller the MFR, the better the processing stability.

TABLE 1

| | Example | | Comparative Example | |
|---|---|---|---|---|
| | 1 | 2 | 1 | 2 |
| Compound to be tested | C-1 | C-2 | — | P-1 |
| MFR (g/minute) | 19.4 | 20.2 | 29.4 | 22.0 |

EXAMPLE 4

Thermal stability test of straight-chain low-density polyethylene

| [Formulation] | |
|---|---|
| Unstabilized straight-chain low-density polyethylene | 100 Parts by weight |
| Hydrotalcite | 0.1 Parts by weight |
| Compound to be tested | 0.05 Parts by weight |

C-1: Compound 1 (produced in Example 1)
C-2: Compound 2 (produced in Example 2)
P-1: 2,10-dimethyl-4,8-di-t-butyl-6-{2-[3-(3-t-butyl-4-hydroxy-5-methylphenyl)propionyloxy]ethoxy}-12H-dibenzo[d,g][1,3,2]dioxaphosphosine Using a 30 mm φ single-screw extruder, the above formulation was repelletized at 250° C. MFR (g/minute) of the resulting pellets was measured at 250° C. under a load of 5000 g for a detention time of 5 minutes by using a melt indexer. The results are shown in Table 2. The smaller the MFR becomes, the better the processing stability.

The resulting pellets were kneaded at 230° C. at 10 rpm for 5 minutes by using a laboplast mill, and then pressed at 250° C. to form a sheet. A YI(Yellow Index) value of the sheet was measured. The results are shown in Table 2.

Evaluation criteria are as follows.

◯: YI=0 to 5

Δ: YI=5 to 10

X: YI>10

TABLE 2

| | Example | | Comparative Example |
|---|---|---|---|
| | 1 | 2 | 1 |
| Compound to be tested | C-1 | C-2 | P-1 |
| MFR (g/minute) | 12.7 | 12.4 | 12.3 |
| Hue | ◯ | ◯ | Δ |

EXAMPLE 5

Thermal stability test of nylon

[Formulation]

| | |
|---|---|
| Unstabilized nylon 6 | 100 Parts by weight |
| Stabilizer to be tested | 0.5 Parts by weight |

C-1: Compound 1 (produced in Example 1)
C-2: Compound 2 (produced in Example 2)
P-1: 2,10-dimethyl-4,8-di-t-butyl-6-{2-[3-(3-t-butyl-4-hydroxy-5-methylphenyl)propionyloxy]ethoxy}-12H-dibenzo[d,g][1,3,2]dioxaphosphosine The above formulation was kneaded by dry blending and then kneaded at 300° C. at 80 rpm for 5 minutes by using a laboplast mill. A torque value after 5 minutes is shown in Table 3. Since nylon 6 is decomposed by deterioration and the torque value is reduced, the higher the torque value after 5 minutes, the better the processing stability.

TABLE 3

| | Example | | Comparative Example | |
|---|---|---|---|---|
| | 1 | 2 | 1 | 2 |
| Compound to be tested | C-1 | C-2 | — | P-1 |
| Torque value (kgf) | 40 | 44 | 22 | 27 |

EXAMPLE 6

Production of 2,10-dimethyl-4,8-di-t-butyl-6-[2-{N-(4-hydroxy-3,5-di-t-butylphenyl)methyl-N-methylamino}ethoxy]-12H-dibenzo[d,g][1,3,2] dioxaphosphosine (compound 3)

In a flask equipped with a thermometer, a stirrer and a condenser, 9.2 g of 2,2'-methylenebis(6-t-butyl-4-methylphenol) and 150 ml of toluene were charged under a nitrogen gas flow. After adding 3.7 g of phosphorous trichloride with stirring, 3.7 g of triethylamine was added, and the mixture was maintained at 80° C. for 4 hours.

After cooling to room temperature, 50 ml of toluene and 7.9 g of 2-[N-(4-hydroxy-3,5-di-t-butylphenyl)methyl-N-methylamino]ethanol were added. Thereafter, 2.9 g of triethylamine was added to the mixture and then the mixture was stirred for 5 hours followed by keeping the mixture at 80° C. for 5 hours.

After cooling to room temperature, the formed hydrochloride of triethylamine was filtered. The filtrate was concentrated and the residue was treated by silica gel chromatography to obtain 6.9 g of a white crystaline compound.

Mass spectrometric analysis (FD-MS): m/z 662
$^1$H-NMR (CDCl$_3$) 1.4(s,18H), 1.5(s,18H), 2.3(s,6H), 2.4 (s,3H), 2.9(t,2H), 3.4(d,1H), 3.6(s,2H), 4.3(d,1H), 4.6(t,2H), 5.1(s,1H), 7.0(s,2H), 7.06(s,2H), 7.13(s,2H)
$^{31}$P-NMR (CDCl$_3$) 128 ppm(s)

EXAMPLE 7

Production of 2,4,8,10-tetra-t-pentyl-12-methyl-6-[2-{N-(4-hydroxy-3,5-di-t-butylphenyl) methyl-N-methylamino)ethoxy]-12H-dibenzo[d,g][1,3,2] dioxaphosphosine (compound 4)

According to the same manner as that described in Example 6 except for using 13.4 g of 2,2'-ethylidenebis(4,6-di-t-pentylphenol), in place of 2,2'-methylenebis(6-t-butyl-4-methylphenol), 3.0 g of a slightly yellowish oily liquid was obtained.

Mass spectrometric analysis (FD-MS): m/z 816
$^1$H-NMR (CDCl$_3$) 0.6(m,12H), 1.2–1.4(m,42H), 1.6(d, 3H), 1.8(q,16H), 2.5(s,3H), 3.1(t,2H), 3.8(s,2H), 4.6(t,2H), 4.8(q,1H), 5.2(s,1H), 7.0(s,2H), 7.2(s,2H), 7.3(s,2H)
$^{31}$P-NMR (CDCl$_3$) 126 ppm(s)

EXAMPLE 8

Production of 2,4,8,10-tetra-t-butyl-6-[2-{N-(4-hydroxy-3,5-di-t-butylphenyl)methyl-N-methylamino)ethoxy]dibenzo[d,f][1,3,2] dioxaphospepine (compound 5)

According to the same manner as that described in Example 6 except for using 13.4 g of 3,3',5,5'-tetra-t-bbutylbiphenyl-2,2'-diol, in place of 2,2'-methylenebis(6-t-butyl-4-methylphenol), 9.0 g of a slightly yellowish oily liquid was obtained.

Mass spectrometric analysis (FD-MS): m/z 732
$^1$H-NMR (CDCl$_3$) 1.3(s,18H), 1.4(s,18H), 1.5(s,18H), 2.1(s,3H), 2.5(t,2H),3.4(s,2H), 3.8(t,2H), 5.1(s,1H), 7.0(s, 2H), 7.1(s,2H), 7.4(s,2H),
$^{31}$P-NMR (CDCl$_3$) 134 ppm(s)

EXAMPLE 9

Production of bis(2,4-di-t-butylphenyl [2-{N-(4-hydroxy-3,5-di-t-butylphenyl)methyl-N-methylamino)ethyl)phosphite (compound 6)

According to the same manner as that described in Example 6 except for using 11.1 g of 2,4-di-t-butylphenol), in place of 2,2'-methylenebis(6-t-butyl-4-methylphenol), 10.2 g of a slightly yellowish oily liquid was obtained.

Mass spectrometric analysis (FD-MS): m/z 734
Elementary analysis(P): 4.16% (Theoretical value 4.22%)

EXAMPLE 10

Production of bis(2,4-di-t-butyl-6-methylphenyl [2-{N-(4-hydroxy-3,5-di-t-butylphenyl)methyl-N-methylamino)ethyl)phosphite (compound 7)

According to the same manner as that described in Example 6 except for using 11.9 g of 2,4-di-t-butyl-6-methylphenol, in place of 2,2'-methylenebis(6-t-butyl-4-methylphenol), 18.3 g of a slightly yellowish oily liquid was obtained.

Mass spectrometric analysis (FD-MS): m/z 762
Elementary analysis(P): 4.00% (Theoretical value 4.06%)

Example 11

Production of 2,10-dimethyl-4,8-di-t-butyl-6-[2-{N-(2-hydroxy-3,5-di-t-butylphenyl)methyl-N-methylamino}ethoxy]-12H-dibenzo[d,g][1,3,2] dioxaphosphosine (compound 8)

In a flask equipped with a thermometer, a stirrer and a condenser, 7.8 g of 2,2'-methylenebis(6-t-butyl-4-methylphenol) and 150 ml of toluene were charged under a nitrogen gas flow. After adding 3.2 g of phosphorous trichloride with stirring, 4.9 g of triethylamine was added, and the mixture was maintained at 80° C. for 4 hours.

After cooling to room temperature, 50 ml of toluene and 6.8 g of 2-[N-(2-hydroxy-3,5-di-t-butylphenyl)methyl-N- methylamino]ethanol were added. Thereafter, 2.4 g of triethylamine was added to the mixture and then the mixture was maintained at 80° C. for 6 hours.

After cooling to room temperature, the formed hydrochloride of triethylamine was filtered. The filtrate was concentrated and the residue was treated by silica gel chromatography to obtain 9.0 g of a white crystaline compound.

Mass spectrometric analysis (FD-MS): m/z 662

$^1$H-NMR (CDCl$_3$) 1.3(s,18H), 1.4(s,18H), 2.3(s,6H), 2.5 (s,3H), 2.9(t,2H), 3.4(d,1H), 3.8(s,2H), 4.3(d,1H), 4.6(t,2H), 6.8(s,1H), 7.05(s,2H), 7.12(s,2H), 7.25(s,1H), 10.8(s,1H), $^{31}$P-NMR (CDCl$_3$)

127 ppm(s)

EXAMPLE 12

Production of 2,4,8,10-tetra-t-pentyl-12-methyl-6-[2-{N-(2-hydroxy-3,5-di-t-butylphenyl) methyl-N-methylamino)ethoxy]-12H-dibenzo[d,g][1,3,2] dioxaphosphosine (compound 9)

According to the same manner as that described in Example 11 except for using 11.4 g of 2,2'-ethylidenebis(4, 6-di-t-pentylphenol), in place of 2,2'-methylenebis(6-t-butyl-4-methylphenol), 3.7 g of a white crystaline compound was obtained.

Mass spectrometric analysis (FD-MS): m/z 816

H-NMR (CDCl$_3$) 0.6(m,12H), 1.2–1.4(m,42H), 1.6(d, 3H), 1.8(q,16H), 2.5(s,3H), 2.9(t,2H), 3.8(s,2H), 4.6(t,2H), 4.9(q,1H), 6.9(s,1H), 7.1(s,2H), 7.2(s,2H), 7.3(s,1H), 10.8 (s,1H)

$^{31}$P-NMR (CDCl$_3$) 127 ppm(s)

EXAMPLE 13

Production of 2,4,8,10-tetra-t-butyl-6-[2-{N-(2-hydroxy-3,5-di-t-butylphenyl)methyl-N-methylamino)ethoxy]-dibenzo[d,f][1,3,2] dioxaphosphepine (compound 10)

According to the same manner as that described in Example 11 except for using 9.4 g of 3,3',5,5'-tetra-t-bbutylbiphenyl-2,2'-diol, in place of 2,2'-methylenebis(6-t-butyl-4-methylphenol), 4.3 g of a white crystaline compound was obtained.

Mass spectrometric analysis (FD-MS): m/z 732

$^1$H-NMR (CDCl$_3$) 1.3(s,18H), 1.4(s,18H), 1.5(s,18H), 2.2(s,3H), 2.6(t,2H), 3.6(s,2H), 3.8(t,2H), 6.8(s,1H), 7.15(s, 2H), 7.2(s,2H), 7.4(s,1H), 10.6(s,1H)

$^{31}$P-NMR (CDCl$_3$) 134 ppm(s)

EXAMPLE 14

Production of bis(2,4-di-t-butylphenyl [2-{N-(4-hydroxy-3,5-di-t-butylphenyl)methyl-N-methylamino}ethyl]phosphite (compound 11)

According to the same manner as that described in Example 11 except for using 9.5 g of 2,4-di-t-butylphenol, in place of 2,2'-methylenebis(6-t-butyl-4-methylphenol), 8.9 g of a slightly yellowish oily liquid was obtained.

Mass spectrometric analysis (FD-MS): m/z 734

$^1$H-NMR (CDCl$_3$) 1.3(s,27H), 1.4(s,27H), 2.3(s,3H), 2.7 (t,2H),3.6(s,2H), 4.2(t,2H), 6.8(s,1H), 7.0–7.3(m,5H), 7.4(s, 2H), 10.8(s,1H), $^{31}$P-NMR (CDCl$_3$) 125 ppm(s)

EXAMPLE 15

Production of N-(4-hydroxy-3,5-di-t-butylphenylmethyl)-2,2'-bis(2,10-dimethyl-4,8-di-t-butyl-12H-dibenzo[d,g][1,3,2]dioxaphosphosine-6-yl-6-oxy)diethylamine (compound 12)

In a flask equipped with a thermometer, a stirrer and a condenser, 20.4 g of 2,2'-methylenebis(6-t-butyl-4-methylphenol) and 150 ml of toluene were charged under a nitrogen gas flow. After adding 8.2 g of phosphorous trichloride with stirring, 12.7 g of triethylamine was added, and the mixture was maintained at 80° C. for 7 hours.

After cooling to room temperature, 50 ml of toluene and 9.3 g of 2,2'-(4-hydroxy-3,5-di-t-butylphenylmethyl) iminodiethanol were added. Thereafter, 6.4 g of triethylamine was added to the mixture and then the mixture was maintained at 80° C. for 7 hours.

After cooling to room temperature, the formed hydrochloride of triethylamine was filtered. The filtrate was concentrated and the residue was treated by silica gel chromatography to obtain 15 g of a white crystaline compound.

Mass spectrometric analysis (FD-MS): m/z 1061

$^1$H-NMR (CDCl$_3$) 1.4(s,36H), 1.5(s,18H), 2.3(s,12H), 3.1(t,4H), 3.3(d,2H), 3.8(s,2H), 4.3(d,2H), 4.5(t,4H), 5.1(s, 1H), 6.9(s,4H), 7.1(s,4H), 7.2(s,2H)

$^{31}$p-NMR (CDCl$_3$) 128 ppm(s)

EXAMPLE 16

Production of N-(4-hydroxy-3,5-di-t-butylphenylmethyl)-2,2'-bis(2,4,8,10-tetra-t-pentyl-12-methyl-12H-dibenzo[d,g][1,3,2] dioxaphosphosine-6-yl-6-oxy)diethylamine (compound 13)

According to the same manner as that described in Example 15 except for using 29.7 g of 2,2'-ethylidenebis(4, 6-di-t-pentylphenol), in place of 2,2'-methylenebis(6-t-butyl-4-methylphenol), 20.7 g of a slightly yellowish crystaline compound was obtained.

Mass spectrometric analysis (FD-MS): m/z 1369

$^1$H-NMR (CDCl$_3$) 0.7(t,24H), 1.2(s,24H), 1.4(s,36H), 1.5 (s,18H), 1.6(d,6H), 1.8(q,16H), 3.1(t,4H), 3.9(s,2H), 4.5(t, 4H), 4.9(q,2H), 5.1(s,1H), 7.0(s,4H), 7.2(s,2H), 7.3(s,4H)

$^{31}$P-NMR (CDCl$_3$) 128 ppm(s)

EXAMPLE 17

Production of N-(2-hydroxy-3,5-di-t-butylphenylmethyl)-2,2'-bis(2,10-dimethyl-4,8-di-t-butyl- 12H-dibenzo[d,g][1,3,2]dioxaphosphosine-6-yl-6-oxy)diethylamine (compound 14)

According to the same manner as that described in Example 15 except for using 9.3 g of 2,2'-(2-hydroxy-3,5-di-t-butylphenylmethyl)iminodiethanol, in place of 2,2'-(4-hydroxy-3,5-di-t-butylphenylmethyl)iminodiethanol, 30.8 g of a white crystaline compound was obtained.

Mass spectrometric analysis (FD-MS): m/z 1061

$^1$H-NMR (CDCl$_3$) 1.3(s,9H), 1.4(s,45H), 2.3(s,12H), 3.2 (t,4H), 3.3(d,2H), 4.1(s,2H), 4.2(d,2H), 4.6(t,4H), 6.9(s,1H), 7.0(s,4H), 7.1(s,4H), 7.2(s,1H), 10.3(s,1H)

$^{31}$P-NMR (CDCl$_3$) 128 ppm(s)

EXAMPLE 18

Production of N-(2-hydroxy-3,5-di-t-butylphenylmethyl)-2,2'-bis(2,4,8,10-tetra-t-pentyl-12-methyldibenzo[d,g][1,3,2]dioxaphosphosine-6-yl-6-oxy)diethylamine (compound 15)

According to the same manner as that described in Example 15 except for using 29.7 g of 2,2'-ethylidenebis(4, 6-di-t-pentylphenol) in place of 2,2'-methylenebis(6-t-butyl-4-methylphenol), and 9.3 g of 2,2'-(2-hydroxy-3,5-di-t-butylphenylmethyl)iminodiethanol in place of 2,2'-(4-hydroxy-3,5-di-t-butylphenylmethyl)iminodiethanol, 21.5 g of a white crystaline compound was obtained.

Mass spectrometric analysis (FD-MS): m/z 1369

$^1$H-NMR (CDCl$_3$) 0.7(t,24H), 1.2–1.4(m,64H), 1.6–1.7 (m,6H), 1.8(m,16H), 3.2(t,4H), 4.2(s,2H), 4.6(t,4H), 4.9(q, 2H), 6.9(s,1H), 7.0(s,4H), 7.2(s,2H), 7.3(s,1H), 10.4(s,1H)

$^{31}$P-NMR (CDCl$_3$) 126 ppm(s)

EXAMPLE 19

Thermal stability test of polypropylene

[Formulation]

| | |
|---|---|
| Polypropylene (block) | 100 Parts by weight |
| Calcium stearate | 0.05 Parts by weight |
| Compound to be tested | 0.05 Parts by weight |

C-3: Compound 3 (produced in Example 6)
C-4: Compound 4 (produced in Example 7)
C-5: Compound 5 (produced in Example 8)
C-6: Compound 6 (produced in Example 9)
C-7: Compound 7 (produced in Example 10)
C-8: Compound 8 (produced in Example 11)
C-9: Compound 9 (produced in Example 12)
C-10: Compound 10 (produced in Example 13)
C-11: Compound 11 (produced in Example 14)
C-12: Compound 12 (produced in Example 15)
C-13: Compound 13 (produced in Example 16)
C-14: Compound 14 (produced in Example 17)
C-15: Compound 15 (produced in Example 18)
P-1: 2,10-dimethyl-4,8-di-t-butyl-6-{2-[3-(3-t-butyl-4-hydroxy-5-methylphenyl)propionyloxy]ethoxy}-12H-dibenzo[d,g][1,3,2]dioxaphosphosine
P-2: 2,4,8,10-tetra-t-pentyl-6-{2-[3-(3,5-di-t-butyl-4-hydroxyphenyl)propionyloxy]ethoxy}-12-methyl-12H-dibenzo[d,g][1,3,2]dioxaphosphosine Using a 30 mm φ sigle-screw extruder, the above formulation was repelletized at 250° C. MFR (g/10 minutes) of the resulting pellets was measured at 250° C. under a load of 2160 g for a detention time of 5 minutes by using a melt indexer. The results are shown in Table 4. The smaller the MFR, the better the processing stability.

TABLE 4

| | Example | | | | | |
|---|---|---|---|---|---|---|
| Exp No. | 1 | 2 | 3 | 4 | 5 | 6 |
| Compound to be tested | C-3 | C-4 | C-5 | C-6 | C-7 | C-8 |
| MFR (g/10 minutes) | 17.2 | 17.3 | 17.2 | 17.8 | 17.8 | 17.2 |

| | Example | | | | | |
|---|---|---|---|---|---|---|
| Exp No. | 7 | 8 | 9 | 10 | 11 | 12 |
| Compound to be tested | C-9 | C-10 | C-11 | C-12 | C-13 | C-14 |
| MFR (g/10 minutes) | 17.3 | 17.2 | 17.7 | 17.5 | 17.4 | 17.6 |

| | Example | Comparative Example | | |
|---|---|---|---|---|
| Exp No. | 13 | 1 | 2 | 3 |
| Compound to be tested | C-15 | — | P-1 | P-2 |
| MFR (g/10 minutes) | 17.3 | 29.4 | 22.0 | 22.5 |

EXAMPLE 20

Thermal stability test of straight-chain low-density polyethylene

[Formulation]

| | |
|---|---|
| Unstabilized straight-chain low-density polyethylene | 100 Parts by weight |
| Hydrotalcite | 0.1 Parts by weight |
| Compound to be tested | 0.15 Parts by weight |

C-3: Compound 3 (produced in Example 6)
C-4: Compound 4 (produced in Example 7)
C-5: Compound 5 (produced in Example 8)
C-6: Compound 6 (produced in Example 9)
C-7: Compound 7 (produced in Example 10)
C-8: Compound 8 (produced in Example 11)
C-9: Compound 9 (produced in Example 12)
C-10: Compound 10 (produced in Example 13)
C-11: Compound 11 (produced in Example 14)
C-12: Compound 12 (produced in Example 15)
C-14: Compound 14 (produced in Example 17)
P-1: 2,10-dimethyl-4,8-di-t-butyl-6-{2-[3-(3-t-butyl-4-hydroxy-5-methylphenyl)propionyloxy]ethoxy}-12H-dibenzo[d,g][1,3,2]dioxaphosphosine
P-2: 2,4,8,10-tetra-t-pentyl-6-{2-[3-(3,5-di-t-butyl-4-hydroxyphenyl)propionyloxy]ethoxy}-12-methyl-12H-dibenzo[d,g][1,3,2]dioxaphosphosine Using a 30 mm φ single screw extruder, the above formulation was re-pelletized at 250° C. The resulting pellets were kneaded under a nitrogen atmosphere at 240° C. at 100 rpm using a laboplast mill. The time required for the torque value to become maximum (gelled-up time, minute) was measured. The results are shown in Table 5. The longer the gelled-up time, the better the processing stability because the crosslinking on kneading is inhibited.

TABLE 4

| | Example | | | | | |
|---|---|---|---|---|---|---|
| Exp No. | 1 | 2 | 3 | 4 | 5 | 6 |
| Compound to be tested | C-3 | C-4 | C-5 | C-6 | C-7 | C-8 |
| MFR (g/10 minutes) | 34.0 | 32.5 | 33.0 | 28.0 | 28.0 | 34.0 |

| | Example | | | | |
|---|---|---|---|---|---|
| Exp No. | 7 | 8 | 9 | 10 | 11 |
| Compound to be tested | C-9 | C-10 | C-11 | C-12 | C-14 |
| MFR (g/10 minutes) | 33.0 | 32.5 | 28.0 | 30.0 | 38.0 |

| | Comparative Example | | |
|---|---|---|---|
| Exp No. | 1 | 2 | 3 |
| Compound to be tested | — | P-1 | P-2 |
| MFR (g/10 minutes) | 5.0 | 16.5 | 17.0 |

EXAMPLE 21

Thermal stability test of nylon

| [Formulation] | |
|---|---|
| Unstabilized nylon 6 | 100 Parts by weight |
| Stabilizer to be tested | 0.5 Parts by weight |

C-3: Compound 3 (produced in Example 6)
C-5: Compound 5 (produced in Example 8)
C-14: Compound 14 (produced in Example 17)
P-1: 2,10-dimethyl-4,8-di-t-butyl-6-{2-[3-(3-t-butyl-4-hydroxy-5-methylphenyl)propionyloxy]ethoxy}-12H-dibenzo[d,g][1,3,2]dioxaphosphosine The above formulation was kneaded by dry blending and then kneaded at 300° C. at 80 rpm for 5 minutes by using a laboplast mill. A torque value after 5 minutes is shown in Table 6. Since nylon 6 is decomposed by deterioration and the torque value is reduced, the higher the torque value after 5 minutes, the better the processing stability.

TABLE 6

| | Example | | | Comparative Example | |
|---|---|---|---|---|---|
| Exp No. | 1 | 2 | 3 | 1 | 2 |
| Compound to be tested | C-3 | C-5 | C-14 | — | P-1 |
| Torque value (kgf) | 44 | 54 | 42 | 22 | 27 |

What is claimed is:

1. A phosphite represented by the formula (I):

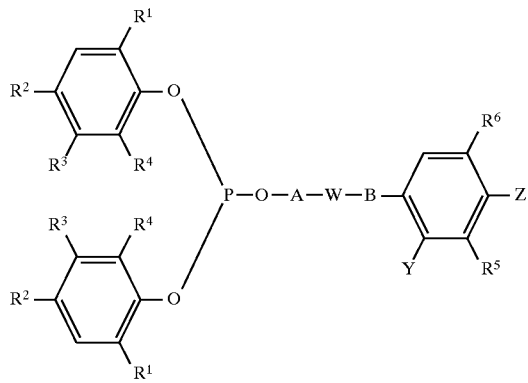

wherein $R^1$, $R^2$, $R^5$ and $R^6$ independently represent a hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group;

$R^3$ represents hydrogen atom or an alkyl group having 1 to 8 carbon atoms;

$R^4$ represents a hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group, or the two $R^4$ together form a direct bond, a group represented by —S— or a methylene group which may optionally be substituted with alkyl having 1 to 8 carbon atoms or cycloalkyl having 5 to 8 carbon atoms;

A represents an alkylene group having 2 to 8 carbon atoms;

W represents a group represented by —O— or a group represented by —NR$^7$
wherein $R^7$ represents a hydrogen atom, an alkyl group having 1 to 8 carbon atoms or a group represented by the following formula (IX):

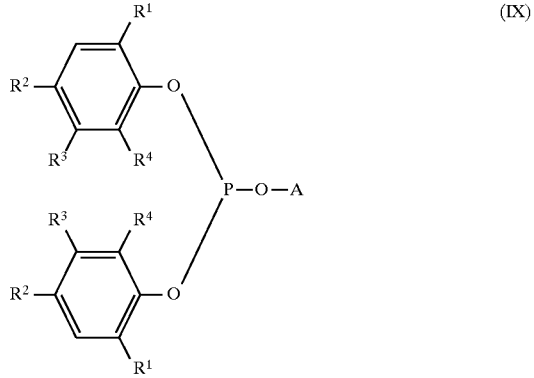

wherein $R_1$, $R^2$, $R^3$, $R^4$ and A are as defined above;

B represents an alkylene group having 1 to 8 carbon atoms; and one of Y and Z represents a hydroxyl group, an alkoxy group having 1 to 8 carbon atoms or an aralkyloxy group having 7 to 12 carbon atoms, and the other one represents hydrogen atom or an alkyl group having 1 to 8 carbon atoms.

2. The phosphite according to claim 1 wherein W represents a group represented by —O—.

3. The phosphite according to claim 1 wherein W represents a group represented by —NR$^7$ wherein $R^7$ is as defined in claim 1.

4. A process for producing the phosphites of claim 2, which comprises reacting a phenol or a bisphenol represented by the formula (II):

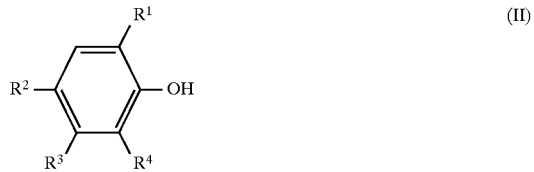

and phosphorous trihalide with an alcohol represented by the formula (III):

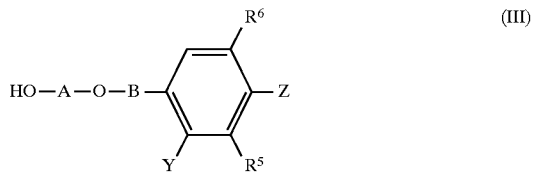

5. A process for producing the phosphites of claim 3, which comprises reacting a phenol or a bisphenol represented by the formula (II):

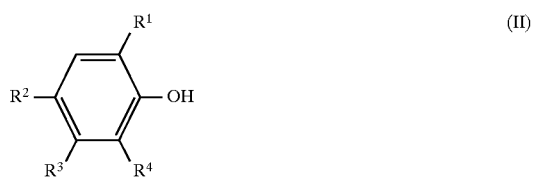

and phosphorous trihalide with an alcohol represented by the formula (IV):

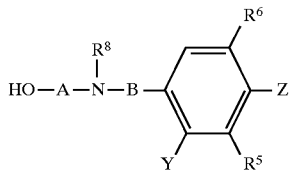 (IV)

wherein $R^8$ is a hydrogen atom, an alkyl group having 1–8 carbon atoms or a group represented by —AOH, and $R^5$, $R^6$, A, B, Y and Z are as defined in claim 1.

6. A stabilizer for organic material, comprising a phosphite of claim 1 as an active ingredient.

7. A method for stabilizing an organic material, which comprises including the phosphite of claim 1 in the organic material.

8. The method according to claim 7, wherein the organic material is a thermoplastic resin.

9. The method according to claim 8, wherein the thermoplastic resin is a polyolefin or an engineering resin.

10. A stabilized organic material composition, comprising an organic material and the phosphites of claim 1.

11. The composition according to claim 10, wherein the organic material is a thermoplastic resin.

12. The composition according to claim 11, wherein the thermoplastic resin is a polyolefin or an engineering resin.

* * * * *